United States Patent
Simpkin et al.

(10) Patent No.: US 10,996,161 B2
(45) Date of Patent: May 4, 2021

(54) SAMPLE RECEPTACLE FOR SPECTROPHOTOMETRY

(71) Applicant: Veriphi Limited, Auckland (NZ)

(72) Inventors: Raymond Simpkin, Auckland (NZ); Amy Susan Garrett, Auckland (NZ); Daniel Wilson, Auckland (NZ); Elliot Thompson-Bean, Auckland (NZ); Greg Shanahan, Auckland (NZ)

(73) Assignee: Veriphi Limited, Auckland (NZ)

( * ) Notice: Subject to any disclaimer, the term of this patent is extended or adjusted under 35 U.S.C. 154(b) by 172 days.

(21) Appl. No.: 16/091,955

(22) PCT Filed: Apr. 7, 2017

(86) PCT No.: PCT/IB2017/051997
§ 371 (c)(1),
(2) Date: Oct. 5, 2018

(87) PCT Pub. No.: WO2017/175180
PCT Pub. Date: Oct. 12, 2017

(65) Prior Publication Data
US 2019/0072481 A1     Mar. 7, 2019

(30) Foreign Application Priority Data

Apr. 8, 2016   (NZ) .................................. 718899
Dec. 13, 2016  (NZ) .................................. 727425

(51) Int. Cl.
*G01N 21/05* (2006.01)
*G01N 21/03* (2006.01)
(Continued)

(52) U.S. Cl.
CPC .............. *G01N 21/05* (2013.01); *B01L 9/06* (2013.01); *G01J 3/0218* (2013.01);
(Continued)

(58) Field of Classification Search
CPC ......... G01N 33/574; G01N 2021/6439; G01N 2021/8416; G01N 2021/8427;
(Continued)

(56) References Cited

U.S. PATENT DOCUMENTS 3,090,861 A    5/1963  Haenni
5,750,998 A    5/1998  Goldman
(Continued)

FOREIGN PATENT DOCUMENTS

GB    1054813 A    1/1967
GB    1582257 A    1/1981

OTHER PUBLICATIONS

International Search Report received in PCT Application No. PCT/IB2017/051997, dated Jun. 5, 2017.
(Continued)

*Primary Examiner* — Michael P Stafira
(74) *Attorney, Agent, or Firm* — Studebaker & Brackett PC

(57) ABSTRACT

Described herein is a receptacle for holding a sample under spectrophotometer analysis comprising: a body, first and second opposing windows separated by a gap to provide a volume for a sample, wherein at least the first opposing window is supported by a first compliant member, and wherein under a force, the first compliant member allows positioning of the first opposing window relative to a first datum to set a desired: a) gap between the first and second opposing windows, and/or b) relative orientation of the first and second opposing windows.

12 Claims, 16 Drawing Sheets

(51) Int. Cl.
    *G01N 21/85* (2006.01)
    *B01L 9/06* (2006.01)
    *G01J 3/02* (2006.01)
(52) U.S. Cl.
    CPC ........ *G01J 3/0267* (2013.01); *G01N 21/0303* (2013.01); *G01N 21/85* (2013.01); *G01N 2021/036* (2013.01); *G01N 2021/0307* (2013.01); *G01N 2021/0389* (2013.01)
(58) Field of Classification Search
    CPC ............... G01N 21/55; G01N 21/6428; G01N 21/6489; G01N 21/8422; G01N 2333/9015; G01N 33/5308; G01N 33/573; G01N 33/6848; G01N 1/18; G01N 2021/0346; G01N 2035/00158; G01N 2035/00237; G01N 2035/1062; G01N 21/05; G01N 21/255; G01N 21/31; G01N 21/33; G01N 21/645; G01N 2201/068; G01N 2333/31; G01N 2333/705; G01N 2333/70503; G01N 2333/90212; G01N 2333/908; G01N 2500/00; G01N 2500/04; G01N 27/26; G01N 27/3271; G01N 27/416; G01N 27/447; G01N 2800/347; G01N 2800/52; G01N 2800/56; G01N 2800/60; G01N 33/5005; G01N 33/5038; G01N 33/5088; G01N 33/53; G01N 33/532; G01N 33/54346; G01N 33/54386; G01N 33/553; G01N 33/564; G01N 33/56961; G01N 33/57438; G01N 33/57473; G01N 33/57484; G01N 33/57488; G01N 33/57492; G01N 33/582; G01N 33/68; G01N 33/6803; G01N 33/6806; G01N 33/6818; G01N 33/6854; G01N 33/6887; G01N 33/6893; G01N 33/94; G01N 35/00029; G01N 35/0099; G01N 35/1009; G01N 35/109; G01N 35/1095; G01N 2035/00881; G01N 2035/0436; G01N 35/026; G01N 2035/0425; G01N 2035/103; G01N 1/31; G01N 2001/315; G01N 2021/0307; G01N 2021/036; G01N 2021/0364; G01N 2021/0389; G01N 2035/00306; G01N 2035/00316; G01N 2035/00752; G01N 2035/1025; G01N 21/0303; G01N 21/1717; G01N 21/253; G01N 21/85; G01N 25/18; G01N 33/487; G01N 2035/00326; G01N 2035/00495; G01N 35/0092; G01N 35/00; G01N 2015/1006; G01N 35/10; G01N 35/00871; G01N 35/1065; G01N 21/25; G01N 35/1072; G01N 33/56983; G01N 15/1475; G01N 2035/00138; G01N 235/00356; G01N 2035/00366; G01N 2035/00425; G01N 2035/0449; G01N 2035/0486; G01N 2035/0491; G01N 2201/024; G01N 2201/04; G01N 33/54366; G01N 35/00069; G01N 35/04; G01N 35/1011; G01N 2015/0073; G01N 2015/008; G01N 2015/1486; G01N 2035/00148; G01N 2035/00435; G01N 2035/0494; G01N 21/27; G01N 2201/12; G01N 33/54306; G01N 33/54313; G01N 33/62; G01N 33/6827; G01N 33/80; G01N 33/92; G01N 35/00623; G01N 21/76; G01N 2035/0094; G01N 21/07; G01N 21/35; G01N 33/491; G01N 1/4077; G01N 2001/4083; G01N 21/03003; G01N 33/50; G01N 1/38; G01N 2021/513; G01N 2035/00277; G01N 21/00; G01N 21/51; G01N 21/59; G01N 21/75; G01N 21/78; G01N 2201/0612; G01N 2201/0853; G01N 2201/121; G01N 33/5302; G01N 15/14; G01N 2001/005; G01N 2021/6417; G01N 2021/6441; G01N 2021/825; G01N 2035/00811; G01N 21/03; G01N 21/21; G01N 21/4133; G01N 21/65; G01N 35/00732; G01N 35/0098; G01N 1/40; G01N 2035/1034; G01N 21/13; G01N 21/6486; G01N 21/68; G01N 21/84; G01N 27/3335; G01N 30/88; G01N 33/0067; G01N 33/54353; G01N 33/66; G01N 15/0205; G01N 15/0806; G01N 15/082; G01N 2013/006; G01N 2015/0065; G01N 2015/0846; G01N 2021/0378; G01N 2021/392; G01N 2021/399; G01N 2021/8835; G01N 2030/8827; G01N 2035/1048; G01N 21/39; G01N 21/6452; G01N 21/6454; G01N 21/6456; G01N 21/66; G01N 2333/005; G01N 2333/185; G01N 233/195; G01N 2333/4709; G01N 2333/48; G01N 2333/525; G01N 2333/5443; G01N 2333/545; G01N 2333/7155; G01N 30/02; G01N 33/48; G01N 33/483; G01N 33/54373; G01N 33/559; G01N 33/566; G01N 33/569; G01N 33/56905; G01N 33/56911; G01N 33/6869; G01N 33/74; G01N 33/86; G01N 33/88; G01N 35/02; B01L 2200/0684; B01L 2300/0861; B01L 2300/1827; B01L 3/502715; B01L 2200/027; B01L 2200/0668; B01L 2200/0673; B01L 2300/0654; B01L 2300/0816; B01L 2300/0864; B01L 2300/0867; B01L 2300/0887; B01L 2300/089; B01L 2400/0406; B01L 2400/0415; B01L 2400/0424; B01L 2400/0427; B01L 2400/043; B01L 2400/0436; B01L 2400/0442; B01L 2400/0448; B01L 2400/0605; B01L 3/0268; B01L 3/502723; B01L 3/502738; B01L 3/502761; B01L 3/502784; B01L 3/502792; B01L 7/52; B01L 7/525; B01L 7/5255; B01L 2200/10; B01L 2300/021; B01L 2300/0681; B01L 2300/1822; B01L 2400/0677; B01L 3/5027; B01L 9/06; B01L 2200/147; B01L 2200/148; B01L 2200/16; B01L 2300/045; B01L 2300/087; B01L 2300/1861; B01L 2400/0481; B01L 2400/0487; B01L 2400/0611; B01L 2400/0683; B01L 9/527; B01L 2300/06; B01L 2300/0627; B01L 2300/0832; B01L 2300/18; B01L 3/0275; B01L 3/52; B01L 2200/12; B01L 2200/14; B01L 2300/0636; B01L 2300/0809; B01L 2300/165; B01L 2300/1805; B01L 2300/1844; B01L 2300/1894; B01L 3/5025; B01L 3/5085;

B01L 3/505; G02B 1/11; G02B 1/113;
G02B 1/18; G01J 3/0218; G01J 3/0267
See application file for complete search history.

(56) References Cited

U.S. PATENT DOCUMENTS

| | | | |
|---|---|---|---|
| 7,369,226 B1 | 5/2008 | Hewitt | |
| 2005/0170522 A1* | 8/2005 | Samsoondar | B01L 3/508 436/169 |
| 2005/0264815 A1 | 12/2005 | Wechsler et al. | |
| 2012/0225021 A1* | 9/2012 | Qian | A61K 49/0002 424/9.6 |
| 2013/0333453 A1 | 12/2013 | Platte et al. | |
| 2015/0119663 A1* | 4/2015 | Lim | A61B 5/14532 600/322 |

OTHER PUBLICATIONS

Written Opinion received in PCT Application No. PCT/IB2017/051997, dated Jun. 5, 2017.

* cited by examiner

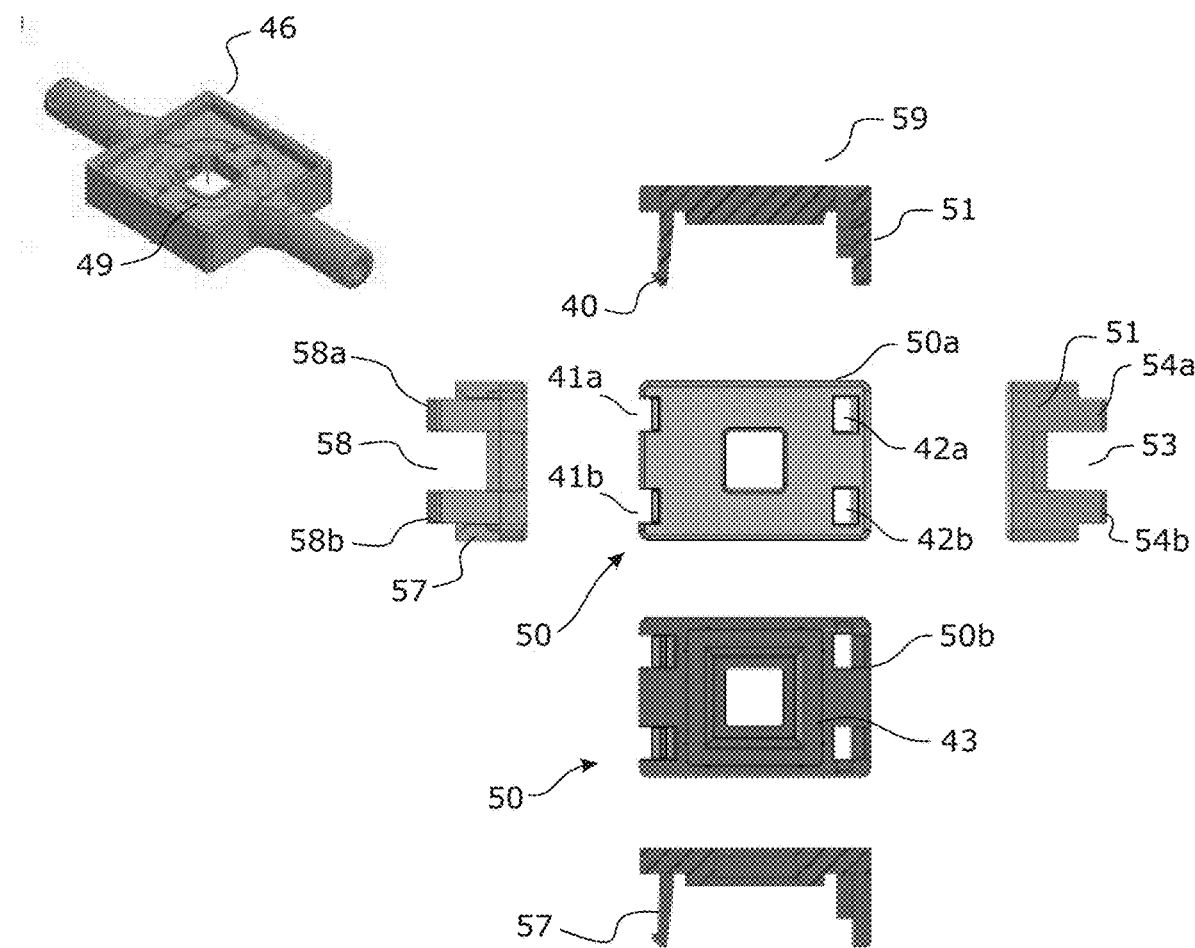
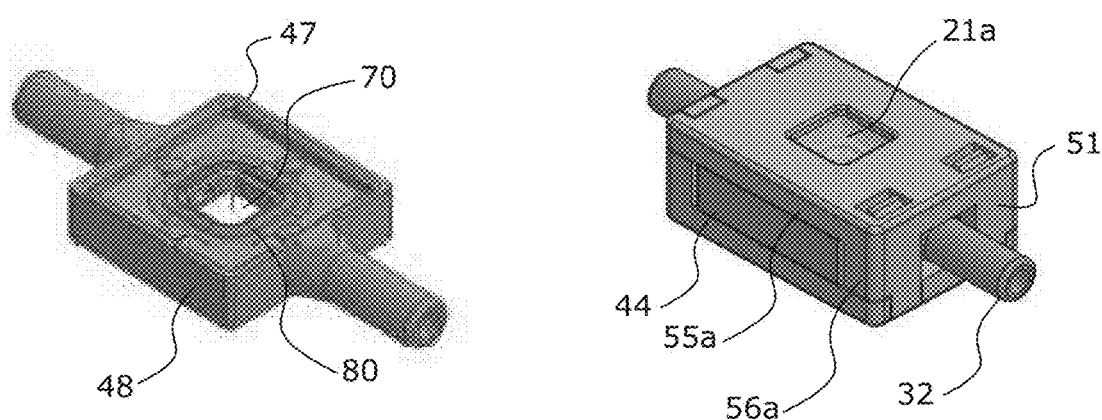
*FIGURE 5*

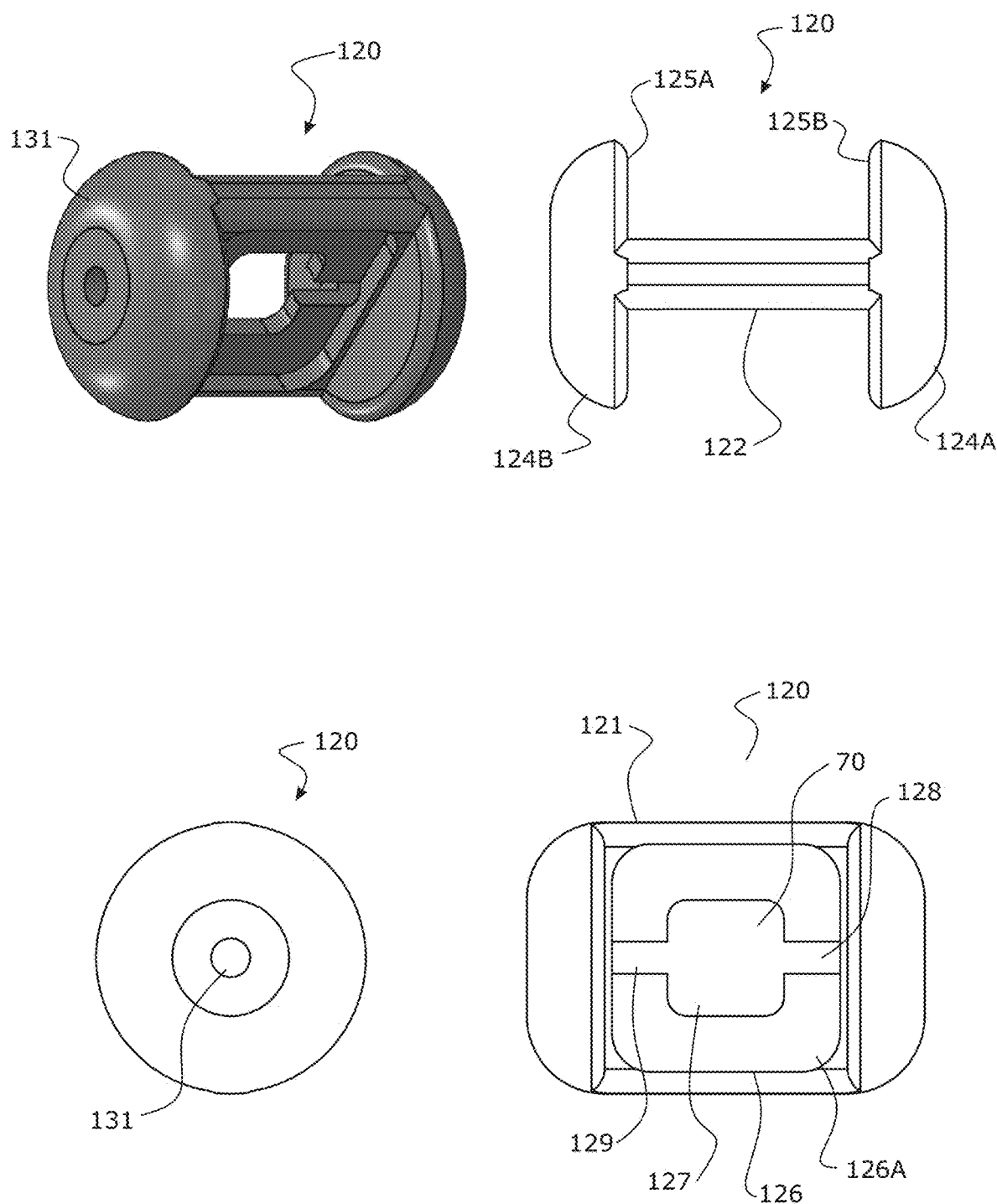
FIGURE 10-I

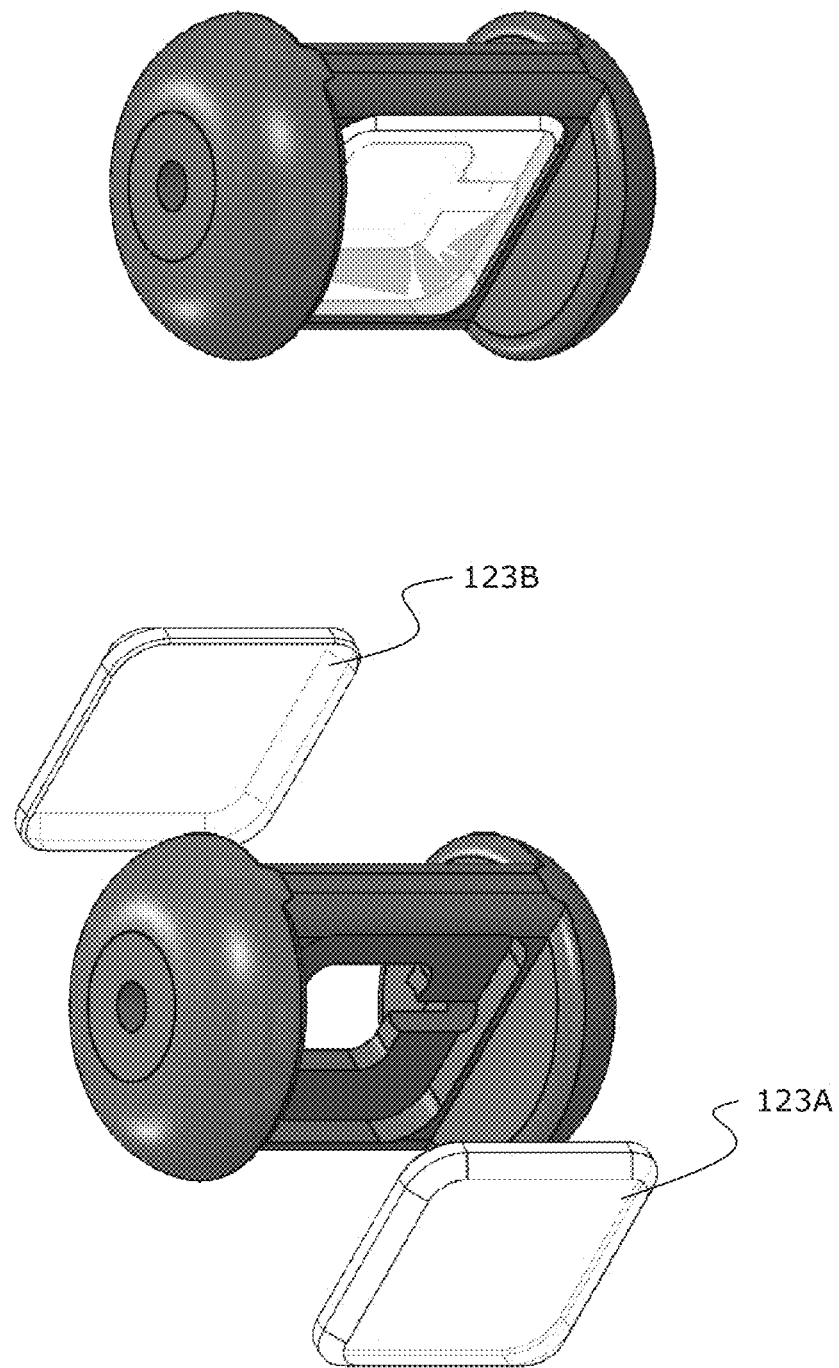
*FIGURE 10-II*

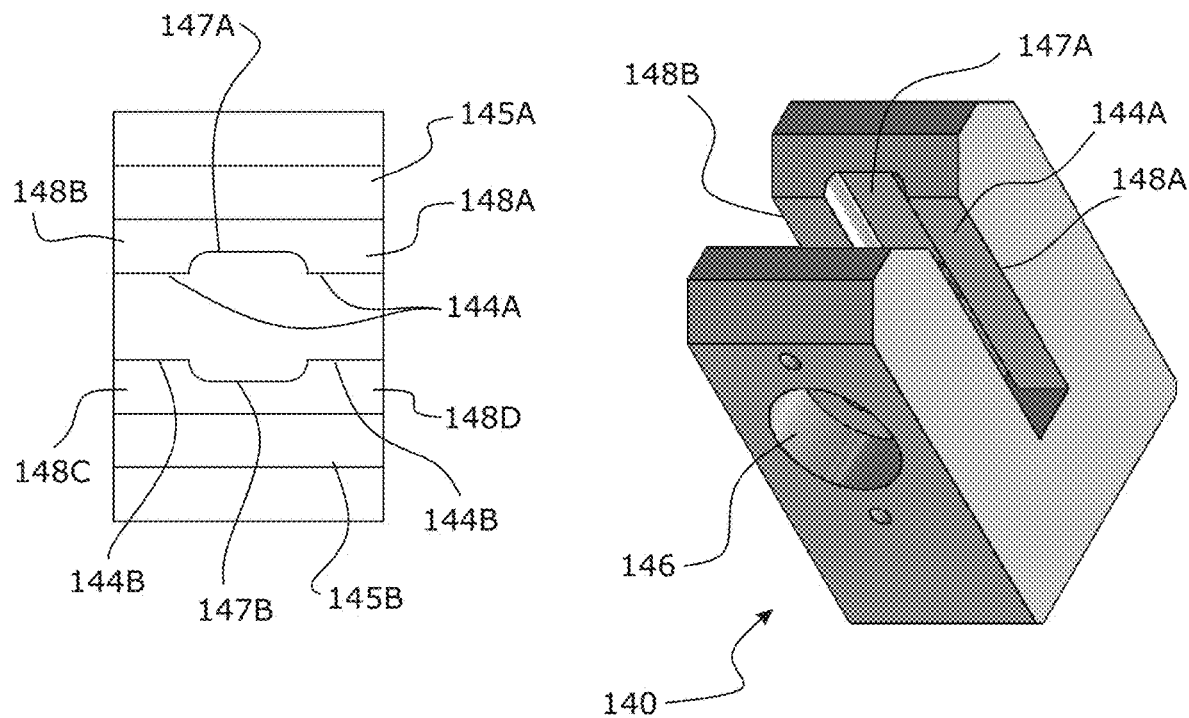
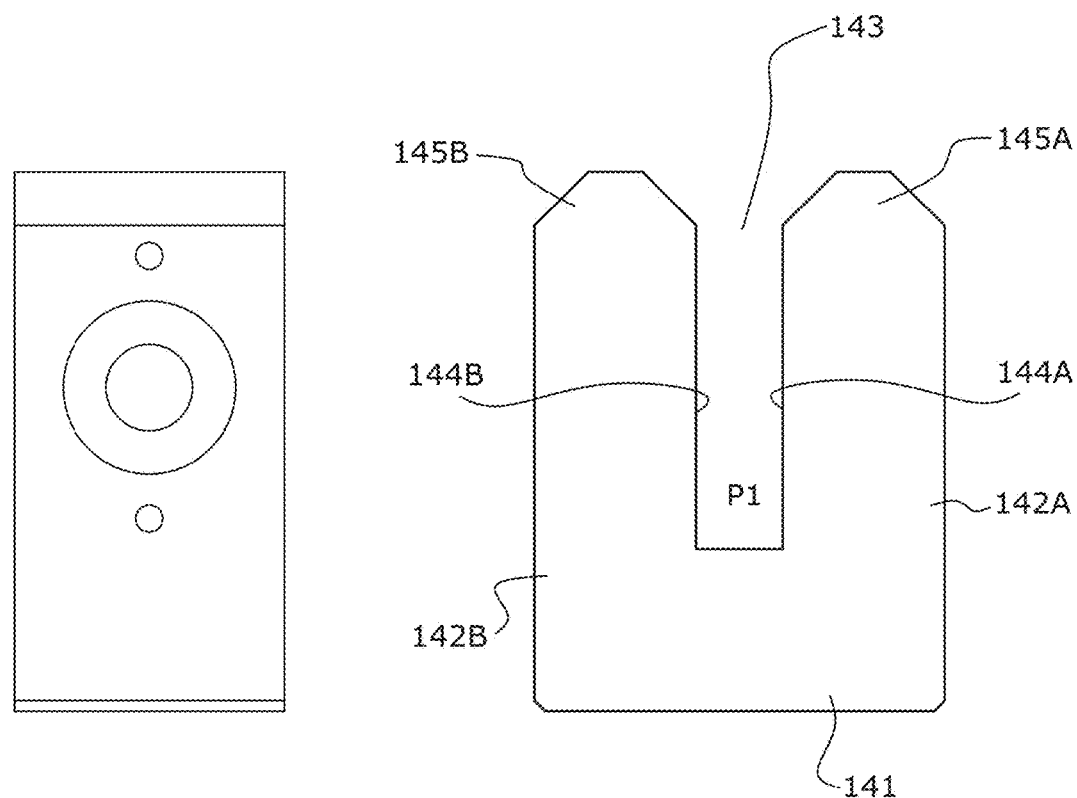
FIGURE 11

SAMPLE RECEPTACLE FOR SPECTROPHOTOMETRY

FIELD OF THE INVENTION

The present invention relates to receptacles and/or corresponding receptacle holders for retaining samples being tested using spectrophotometry.

BACKGROUND TO THE INVENTION

Spectrophotometry enables analysis of samples, such as drugs, by providing incident light on the sample and analysing the light that is reflected from and/or transmitted through the sample.

SUMMARY OF INVENTION

It is an object of the present invention to provide a receptacle and/or corresponding receptacle holder for a sample for using in spectrophotometry.

It is desirable that a receptacle for spectrophotometry testing is disposable, so that a new receptacle is used for each test. It has been determined that the receptacle should be designed so if different receptacles are used in different tests, there is still repeatability over multiple tests, even if there are variances in manufacturing tolerances of each receptacle.

In one aspect the present invention may comprise a receptacle for holding a sample under spectrophotometer analysis comprising: a body, first and second opposing windows separated by a gap to provide a volume for a sample, wherein at least the first opposing window is supported by a first compliant member, and wherein under a force, the first compliant member allows positioning of the first opposing window relative to a first datum to set a desired a) gap between the first and second opposing windows, and/or b) relative orientation of the first and second opposing windows.

Optionally the second opposing window is supported by the first or a second compliant member, wherein the first and/or second compliant member allows positioning of the second opposing window under force at the first datum and/or a second datum to set the desired a) gap between the first and second opposing windows, and/or b) relative orientation of the first and second opposing windows.

In another aspect the present invention may comprise a receptacle for holding a sample under spectrophotometer analysis comprising: a body, first and second opposing windows separated by a gap to provide a volume for a sample, wherein said first and second opposing windows are supported by said body, and wherein under a force, the body allows positioning of the windows relative to a datum set to set a desired: a) gap between the first and second opposing windows, and/or b) relative orientation of the first and second opposing windows.

Optionally the first and/or second datum is in the housing.

Optionally the first and/or second datum is external to housing.

Optionally the receptacle further comprises an inlet and an outlet for ingress and egress of a sample into and out of the volume.

Optionally the receptacle further comprises a frame or other support, wherein: the first opposed window is supported by the first compliant member on the frame, and/or the second opposed window is supported by the first and/or second compliant member on the frame.

Optionally the volume is in the frame and the inlet and outlet are coupled to the volume.

Optionally the receptacle further comprises first and second apertures on opposing sides of the housing to expose the first and second windows.

Optionally the receptacle further comprises a jig (holder) for receiving the housing, wherein the jig comprises the first datum and/or the second datum.

Optionally when the housing is received in the jig, the first and/or second window are positioned at the first and/or second datum under force of a sample in the volume.

Optionally when the housing is received in the jig, the first and/or second window are positioned at the first and/or second datum under force of the jig moving the first and/or second datum.

Optionally the first and/or second datum is/are stops that the first and/or second windows abut against under force.

Optionally:
the desired gap is 2 mm+/−0.2 mm,
each window is 3 mm+/−0.1 mm thick, and/or
the relative orientation between the first and second opposing windows is parallel or substantially parallel, preferably to within +/−0.05 degrees,
the orientation of window surfaces is parallel or substantially parallel and is or is substantially at right angles to incident radiation in use, optionally within 3 minutes of an arc.

In another aspect the present invention may comprise a receptacle for a sample comprising first and second opposing windows separated by a gap for holding a sample wherein the first and/or second opposing windows are supported by a compliant member such that under force the first and second opposing windows are positioned at a datum to set a required gap and orientation for analysis of a sample in the gap.

Optionally the first and/or second datum is/are fabricated using a process that allows for a higher degree of tolerance than the process used to fabricate the first and/or second window, first and/or second compliant member, and/or support.

In another aspect the present invention may comprise a spectrophotometer analyser comprising a source to emit electromagnetic radiation at a sample, a detector to receive electromagnetic radiation affected by the source and a processor to characterise the sample from the detector output, wherein the sample is held in a receptacle according to any one of the paragraphs above.

In another aspect the present invention may comprise a spectrophotometer analyser comprising a source to emit electromagnetic radiation at a sample, a detector to receive electromagnetic radiation affected by the source, receptacle according to any paragraph above and a processor to characterise the sample from the detector output, wherein the sample is held in the receptacle.

In another aspect the present invention may comprise a holder for receiving a receptacle according to any one of the paragraphs above.

In another aspect the present may comprise a holder for receiving receptacle for holding a sample under spectrophotometer analysis, wherein the receptacle comprises: a body, and first and second opposing windows separated by a gap to provide a volume for a sample, wherein at least the first opposing window is supported by a first compliant member, and wherein the holder is operable to provide a force to the receptacle such that the first compliant member allows positioning of the first opposing window relative to a first datum to set a desired a) gap between the first and second opposing windows, and/or b) relative orientation of the first and second opposing windows.

Optionally the second opposing window is supported by the first or a second compliant member, wherein the first and/or second compliant member allows positioning of the second opposing window under force at the first datum and/or a second datum to set the desired a) gap between the first and second opposing windows, and/or b) relative orientation of the first and second opposing windows.

Optionally the first and/or second datum is in the holder and optionally moveable by the holder.

Optionally when a receptacle is received in the holder, the first and/or second window are positioned at the first and/or second datum under force of a sample in the volume.

Optionally when the receptacle is received in the holder, the first and/or second window are positioned at the first and/or second datum under force of the holder moving the first and/or second datum.

Optionally the first and/or second datum is/are stops that the first and/or second windows abut against under force.

Optionally the receptacle:
the desired gap is 2 mm+/−0.2 mm,
each window is 3 mm+/−0.1 mm thick, and/or the relative orientation between the first and second opposing windows is parallel or substantially parallel, preferably to within +/−0.05 degrees, the orientation of window surfaces is parallel or substantially parallel and is or is substantially at right angles to incident radiation in use, optionally within 3 minutes of an arc.

In another aspect the present invention may comprise a holder for receiving a receptacle for a sample comprising first and second opposing windows separated by a gap for holding a sample wherein the first and/or second opposing windows are supported by a compliant member such that under force the first and second opposing windows are positioned at a datum to set a required gap and orientation for analysis of a sample in the gap.

Optionally the first and/or second datum is/are fabricated using a process that allows for a higher degree of tolerance than the process used to fabricate the first and/or second window, first and/or second compliant member, and/or support.

In another aspect the present invention may comprise a holder for receiving receptacle for holding a sample under spectrophotometer analysis, wherein the receptacle comprises: a body, and first and second opposing windows separated by a gap to provide a volume for a sample, wherein at least the first opposing window is supported by a first compliant member, and wherein the holder comprises a first jig member and a second jig member for receiving the receptacle and the first and/or second jig member are operable to provide a force to the receptacle such that the first compliant member allows positioning of the first opposing window relative to a first datum (optionally on the first or second jig member) to set a desired a) gap between the first and second opposing windows, and/or b) relative orientation of the first and second opposing windows.

In another aspect the present invention may comprise a receptacle for holding a sample under spectrophotometer analysis comprising: a compliant support for first and second windows an opening in the support, and first and second windows on the support forming a volume with the opening, wherein under a force, the compliant support allows positioning of at least the first window relative to a first datum to set a desired a) gap between the first and second windows, and/or b) relative orientation of the first and second windows.

Optionally under a force, the compliant support allows positioning of the second window relative to a second datum to set the desired a) gap between the first and second windows, and/or b) relative orientation of the first and second windows.

Optionally the compliant support comprises a support frame formed of compliant material.

Optionally the compliant support comprises a rigid support frame with a compliant covering.

In another aspect the present invention may comprise a receptacle wherein: the desired gap is 2 mm+/−0.2 mm, each window is 3 mm+/−0.1 mm thick, and/or the relatively orientation between the first and second windows is parallel or substantially parallel, preferably to within +/−0.05 degrees, the orientation between window surfaces is parallel or substantially parallel, optionally within 3 minutes of an arc.

Optionally the receptacle further comprising end portions at each end of the compliant support.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

BRIEF DESCRIPTION OF THE DRAWINGS

Possible embodiments will be described, of which:

FIG. 5 shows the first embodiment of the sample receptacle in more detail

FIG. 10-I shows a further alternative embodiment of a sample receptacle.

FIG. 10-II shows a perspective view of the embodiment as seen in FIG. 10-I.

FIG. 11 shows an alternative jig for use with the further embodiment of the sample receptacle as shown in FIGS. 10-I to 10-II.

DETAILED DESCRIPTION

System Overview

Figure 1:
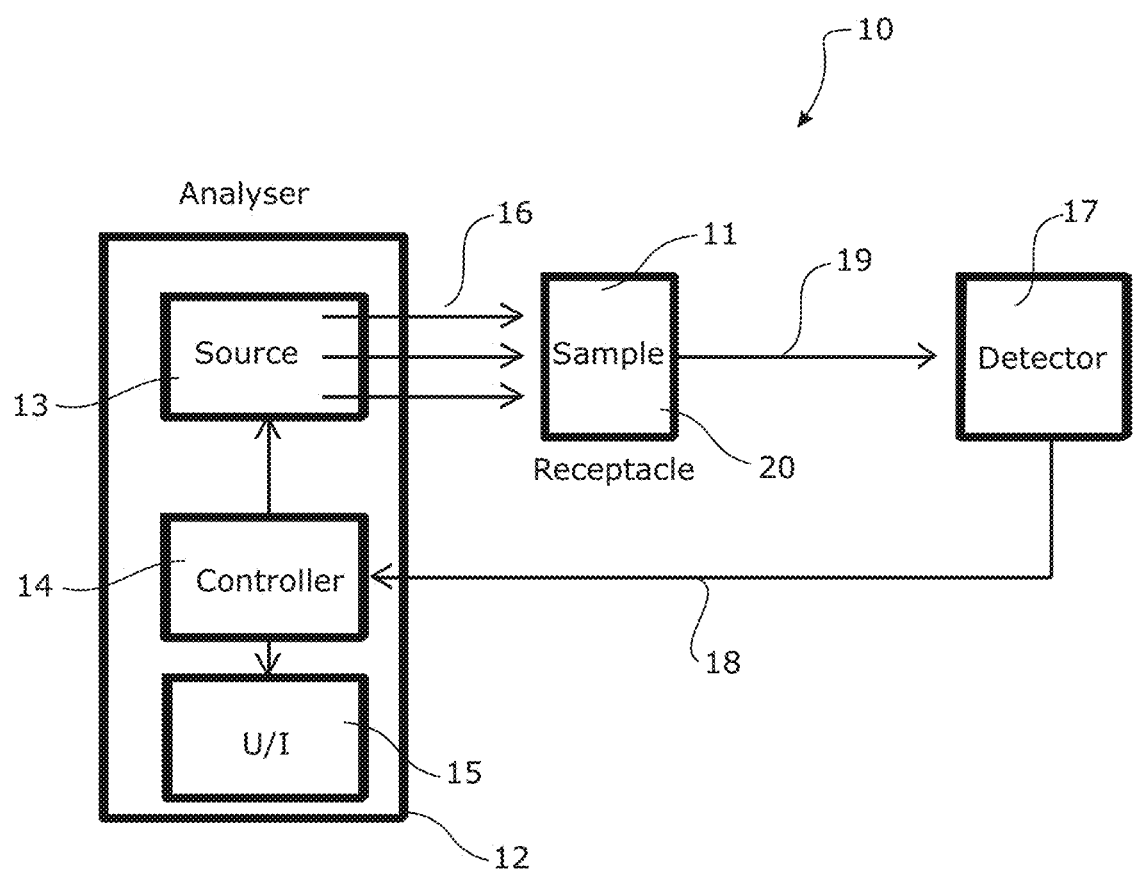
FIG. 1 shows in schematic form a spectrophotometry system for characterising a sample comprising a spectrophotometer and sample receptacle.

FIG. 1 shows in general form, a spectrophotometry system 10 for characterising a sample 11, such as a drug sample, chemical sample, biological sample or any other substance that requires characterisation. Characterising can comprise verifying a sample (that is, confirming whether it is or is not a particular substance) or identifying a sample (determining what type of substance it is, optionally from a set of possible substances), for example. Such a system 10 could be used in any suitable healthcare situation where a drug sample needs to be characterised. For example, it could be used in pharmacology unit of a hospital, where drugs are mixed prior to dispatch, or it could be used bedside in a hospital to check a drug prior to administering the drug to a patient via a IV bag/line or via syringe, or in a doctor's surgery to check a drug prior to an injection. The system could also be used in other medical or healthcare situations. Alternatively, such a system 10 could be used in an entirely different industry where a sample of a drug, a compound, a chemical, a biological or other sample needs to be characterised.

The spectrophotometry system 10 comprises a spectrophotometer analyser ("analyser") 12. The analyser has an electromagnetic radiation source 13, such as one or more lasers, a controller 14 and an input/output interface 15. The controller can be or comprise a microprocessor or other processor that can provide control and processing capability. The analyser 10 generates one or more electromagnetic radiation beams 16 (such as light), by using the controller 14 to operate the source 13 (e.g. lasers) to emit beams 16 through a channel (such as free space, waveguide, fibre optic cable or the like) at various wavelengths towards the sample 11. FIG. 1 shows multiple beams, although one beam could be emitted containing electromagnetic radiation at multiple wavelengths. The analyser 12 also has one or more detectors 17 for receiving electromagnetic radiation 19 via another channel (such as free space, waveguide, fibre optic cable or the like—see, e.g. FIG. 6) after it has passed through the sample 11. The detector 17 feeds output signals 18 back to the controller 14 in the analyser 12. The controller characterises the sample 11 using the output signals 18, and optionally other information such as reference information. The controller 14 then indicates on an output interface 15 (such as a screen) the characterisation of the sample—for example, it identifies the sample, or verifies whether or not the sample is what the user thinks it is and/or determines the concentration of the sample. The system 10 (including the analyser 12 components 13, 14, 15 and other components 20, 17) could be integrated or formed as separate components.

The spectrophotometry system, could be, for example, the system as described in any one of the following patent publications, the contents of which are incorporated herein by reference in their entirety.

U.S. Pat. No. 8,512,279
PCT application WO2012/138236
PCT application WO2013/191566
PCT application WO2014/054022

It will be appreciated that the spectrophotometry systems described above are by way of example only. The sample receptacle embodiments described herein could be used with those or any other type of spectrophotometer systems, for characterising including verifying drugs, chemicals, biologicals, compounds or any other types of samples.

General Overview of Receptacle and Parameter Tolerances

During the characterisation process, the sample 11 is held in a receptacle 20 in accordance with any of the embodiments described herein. Such a receptacle 20 may be formed or integrated as part of the analyser 12, or overall spectrophotometry system 10, or could be retrofitted or inserted/removed from the analyser 12/system 10 or be a separate component that is used with the analyser 12/system 10.

Figure 2:
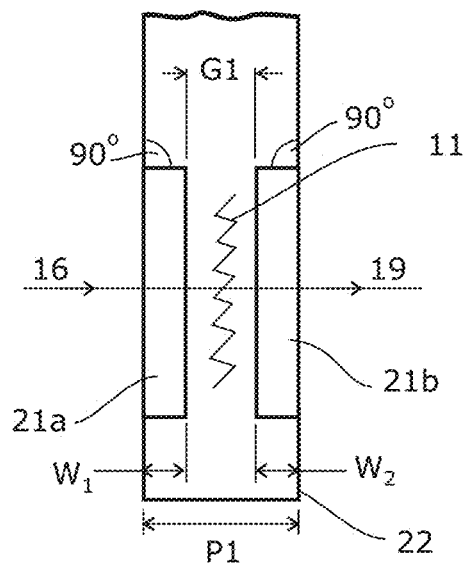
FIG. 2 shows in schematic form a general embodiment of sample receptacle.

FIG. 2 shows a receptacle 20 in diagrammatic functional form. In general terms, the receptacle is a container 22 that can hold a liquid or other sample 11 under test. The container comprises opposing transparent windows 21a, 21b or similar, such that the sample 11 can reside between the windows 21a, 21b. The windows can be made from any material that allows electromagnetic radiation to pass there through without being absorbed by the material at the absorbance peaks of the liquid sample being analysed. Suitable materials include glass, quartz and the like.

Electromagnetic radiation 16 can be emitted to the first window 21a (the angle of incidence being at right angles to the window surface), where it travels through the window, through the sample 11 and out through the opposing window 21b (the angle of incidence being at right angles to the window surface) (see beam 19) the detector 17. The receptacle comprises the following core receptacle parameters.

Windows with thickness W1, W2.

Gap between the windows of thickness G1 (leading to a sample fluid/air thickness of the same).

An overall path length P1, which is the total of the window thicknesses W1, W2 and the gap G1.

Windows with opposite surfaces that are parallel to each other.

Opposing windows that are parallel to each other (or have another desired relative orientation), and arranged with an orientation so that incident electromagnetic radiation hits perpendicular to the window surfaces.

The apparatus is arranged so that the angle of incidence of incoming/incident radiation is at right angles/perpendicular relative to the window surfaces. The importance being that the light incident on the first window travels through the volume and then exits from the second window on a straight line/path that does not suffer deviation. This is largely achieved by the angle of incidence of light hitting the first window at right angles or substantially at right angles and then exiting the second window again at right angles or substantially at right angles following that same path.

Note, other parameters of the receptacle exist, but the above parameters influence repeatability, as described below.

These parameters can be determined according to the particular operating wavelength range of source radiation 16 that the system 10 uses. It has been determined that to accurately characterise a sample 11 repeatedly using a spectrophotometer analyser 12 (such as those referenced above), it is highly desirable that the above receptacle parameters are maintained to within a desired tolerance/precision for each test. If the receptacle 20 is changed, it is important for the next receptacle in use to have the same properties to within the required tolerance/precision. If subsequent sample receptacles 20 for subsequent tests have properties within the required tolerance, this assists with accurate repeatability of characterisation across many samples, by providing good discrimination between samples, and accuracy. This also enables tolerances due to temperature and other external factors to be compensated for.

For example, when operating with source wavelengths 16 in the 1300 nm to 2000 nm range for testing drugs as described in the aforementioned patent publications, the following receptacle parameters and tolerances are desired.

Each window has a thickness W1, W2 of 3 mm+/−0.1 mm

Each window has two opposing surfaces that are parallel, preferably to within 3 minutes of an arc and a flatness to less than 4 Newton fringes Each window is parallel to the other opposing window, preferably to within +/−0.05 degrees The gap length/thickness G1 between windows is 2 mm+/−0.2 mm The total path length P1 (through both windows and the gap) is 8 mm+/−0.4 mm Other dimensions would be suitable for other wavelengths. More generally, the considerations for the dimensions are set out below.

The gap G1 dimension is determined to provide a desirable level of attenuation of the light signal as it goes through; and provide a desirable volume for the sample. If the gap G1 is too small, there is not enough light signal due to small volume to measure the sample and if G1 is too large then too much noise. The desired gap length G1 of 2 mm for 1300 nm to 2000 nm range is determined based on determining the greatest transmittance contrast between the saline (or other based liquid) and the drug dissolved in saline (more generally, base liquid) across the 1300 nm to 2000 nm range. This transmittance contrast has an optimum gap length G1. If the gap length is too small then the transmittance contrast is not strong enough. Similarly, if the gap length G1 is too long the transmittance contrast is attenuated and not strong enough. A gap length G1 is selected to provide the strongest transmittance contrast with minimal attenuation to the signal. The desired tolerance for gap length G1 is 2 mm+/−0.2 mm. However, optionally, the gap length G1 can be varied between the ranges of 1-4 mm+/−0.8 mm, or between 1.5-3.5 mm+/−0.8 mm, depending on the base liquid and/or the wavelength range. The tolerance can further be stepped back down to +/−0.5 mm.

The desired window thickness W1, W2 needs to be thick enough to make the optical thickness of each window sufficiently different from that of gap length G1 in order to differentiate and separate out the peaks associated with the saline fluid (or other base liquid), and the peak of the drug sample dissolved in the saline fluid (base liquid). The desired window thickness W1, W2 also needs to be thin enough to avoid excessive attenuation of the light. The desired window thickness W1, and W2 of 3 mm is therefore selected on the basis that it meets the requirements discussed here for 1300 to 2000 nm range. W1 and W2 are also dimensioned such that the distances (thicknesses) of the windows are the same or within similar tolerances to one another. This provides symmetry. So the tolerances of a set of windows (2 windows) being the same distances is around +/−0.2 mm, however the individual window thicknesses can be 3 mm+/−0.5 mm. The equality of the window thicknesses is desirable to ensure that there are not different peaks associated with different window thicknesses as this will affect processing or output data and therefore potentially compromise the drug verification or identification.

The above are just exemplary, and the desired dimensions could vary, even for the 1300 nm to 2000 nm range. For example, the desired gap length G1 might be selected to be between about 1 mm and about 4 mm+/−0.8 mm, or selected to be between about 1.5 mm and about 3.5 mm, +/−0.8 mm, or selected to be between about 1.5 mm and about 3.0 mm, +/−0.8 mm. depending on the base liquid and/or the wavelength range. Similarly, desired window thickness W1, W2 might be selected to be between about 2 mm and about 6 mm+/−0.8 mm. Commensurate ranges would apply to P1.

From practical perspectives, the dimensions defined by the height and length of W1 and W2 with the distance of G1 (and their relative arrangement) provide a cavity to contain a sufficient amount of fluid, to ensure that the fluid retained in the cavity has sufficient drug quantity in the cavity to interfere with the light, albeit the light only sees a narrow band. Also the thickness of W1 and W2 must be mechanically robust during use and to handle being put into the jig.

The total path length P1 is the arithmetic summation of window thickness W1, W2, and gap length G1. The desired window thickness of W1 and W2 is 3 mm+/−0.1 mm, while the desired gap length G1 is 2 mm+/−0.2 mm. The desired total path length P1 is therefore 8 mm+/−0.4 mm.

Orientation of opposing windows taken this to mean that the orientation is such that the windows are parallel and that the light that is incident on the windows is as close to 90 degrees (angle of incidence) as possible or within the 3 minutes of deviation. It is highly desirable that the windows are parallel with one another but also as close to being perpendicular relative to the incident electromagnetic radiation in order for the light source to beam through the sample at right angles. That is, the angle of incidence of the light is at right angles. The apparatus is arranged so that the angle of incidence of incoming/incident radiation is at right angles/perpendicular or substantially right angles/perpendicular relative to the window surfaces.

It will be appreciated that the desired parameter values and tolerances will change depending on the operating wavelengths, and the nature of the samples under test. The above are example parameters for the 1300 nm to 2000 nm range, and are exemplary for those wavelengths only.

For example, it is desirable that the drug sample being tested is dissolved in saline. In this instance, the selection of a wavelength in the 1300 nm to 2000 nm range produces spectral information that is useful in verifying or identifying drug components in the drug sample under test. This requires a desired total path length P1 to be 8 mm+/−0.4 mm. The disclosure of these figures heretofore are intended to illustrate the present invention by way of example.

However, it is also possible to use this invention for detecting spectral characteristics in drug samples that are not saline based and/or detecting spectral information outside of the 1300 nm to 2000 nm range. In such a situation, the wavelength of the emitting radiation and the total path length P1 are adjusted accordingly that allows the present invention to be used as part of a spectrophotometry system in a manner similar to the disclosure in the patent publications referenced above.

It is desirable that the receptacle 20 is disposable (consumable) or contains disposable (consumable) parts/components. That is, after each use, the receptacle or part(s) thereof can be thrown away and replaced for each new test. This improves accuracy and prevents cross contamination, plus provides a range of other benefits. To make the receptacle or part thereof disposable, it must be cheaply, and easily manufacturable to be commercially viable. However, processes that satisfy these manufacturing needs, often do not fabricate components to the required degree of tolerance/precision to meet the receptacle parameter requirements noted above. Manufacturing processes that provide the required precision are often too expensive to use for fabricating disposable parts.

Embodiments described herein overcome this problem by enabling fabrication of receptacles with cheap/easy to manufacture disposable parts, while still allowing for the required precision of the core receptacle parameters. Embodiments described herein achieve that by having certain parts of the receptacle (and/or associated apparatus) that are reusable and manufactured to a higher level of tolerance/precision, and other parts of the receptacle (and/or associated apparatus) that are disposable and manufactured to a lower level of tolerance/precision. The components that are manufactured to a high level of tolerance/precision enable the required precision to be met, either through providing the ability to compensate for tolerances of other components that fall outside the desired range and/or through providing the required tolerances/precision themselves. The embodiments described can be used for a receptacle designed with core parameters and tolerances to operate at any wavelengths—not just those described above. The above parameter values are just used as an example.

Example Embodiments of Receptacles

Figure 7:
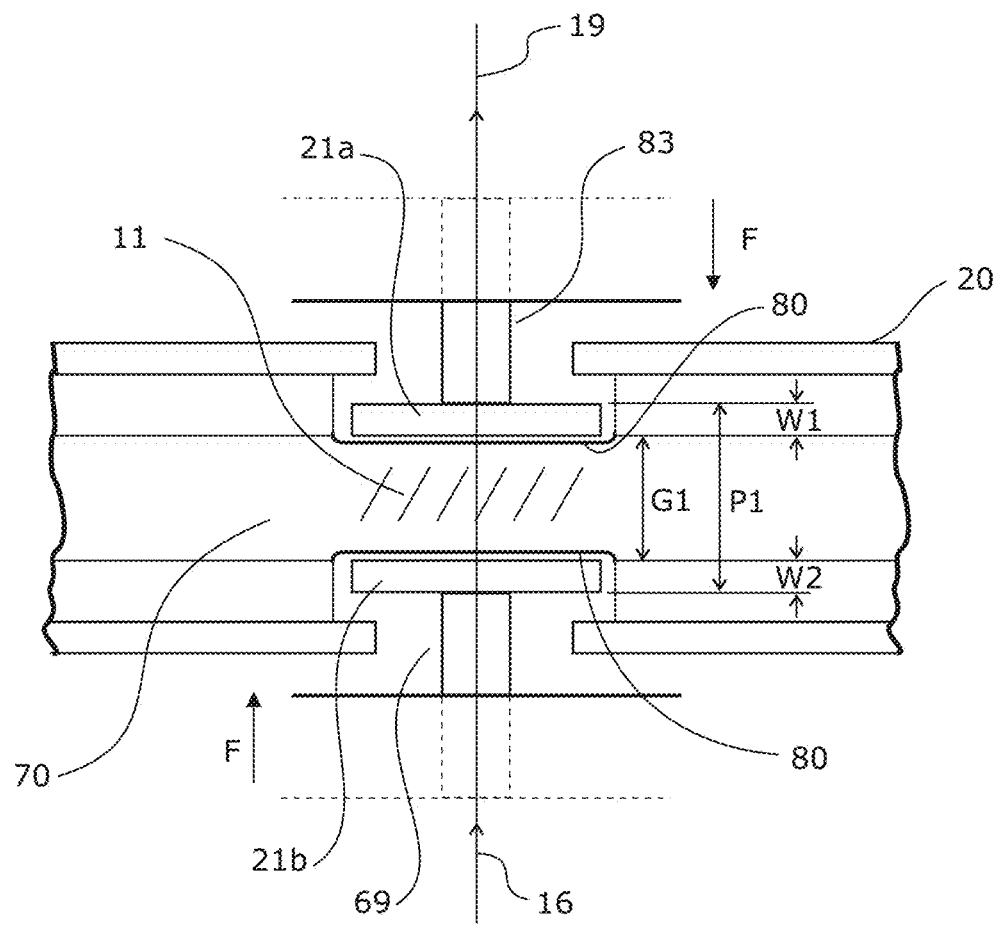
FIG. 7 shows the embodiment in diagrammatic form.

Referring to FIG. 7, as a general example (not to scale), a sample receptacle 20 comprises: a container 20 with a volume 70 for retaining the sample 11 undergoing characterisation, two parallel windows 21a, 21b positioned either side of the volume that are transparent to the electromagnetic radiation 16, 19 being used for the characterisation. The windows are separated by a gap G1 which forms at least part of the volume. An adjustment mechanism/compensation mechanism is provided to enable manipulation of the windows to position them parallel to the required tolerance and separated by the desired distance G1 to the required tolerance to compensate for manufacturing tolerances in the window thickness W1, W2, air gap G1, path length P1 and window orientation. The mechanism uses a datum(s) 69, 83 and a compliance member(s) 80 to set the window orientation and path length P1 to compensate for any manufacturing tolerances. A force F coerces the windows 21a, 21b to the datum 69, 83 or vice versa, the movement being allowed for by the compliant member(s) 80. The datum(s) 69 83 can be set to the required path length P1 to within the required tolerance, which compensates for errors in the gap G1 and/or windows thickness W1, W2 during manufacture. For example, in the general embodiment, the adjustment/compliance mechanism comprises a gasket 80 or other flexible or compliant component that bears against the windows 21a, 21b, an external force F for bearing on the compliant component 80 and/or window 21a, 21b to manipulate its position, and a datum 69, 83 for positioning the windows correctly. The datum could be part of or separate to the receptacle, and the receptacle might be used in combination with other apparatus. As an example, the receptacle can be placed in a holder for testing, where the holder provides the datum and/or the force, or generally assists with configuring the receptacle so that the required tolerances are achieved for test.

Figure 3:
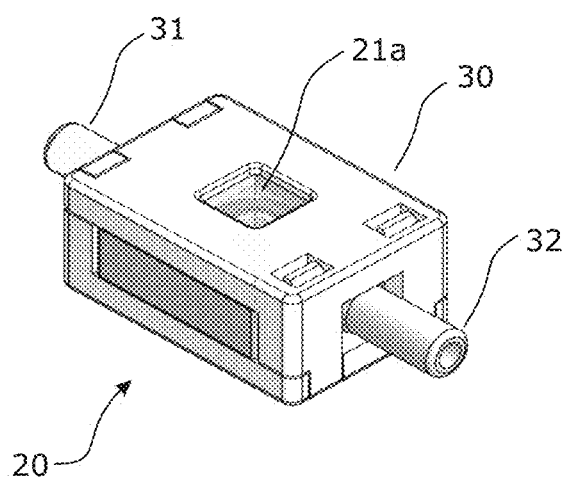
FIG. 3 shows a first embodiment of a sample receptacle.

One example embodiment of the receptacle 20 will now be described. It will be described in the context of testing of drug samples mixed in an IV bag in the pharmacology unit of a hospital, although it will be appreciated that this or other embodiments described herein are not restricted to use just in this context. Referring to FIG. 3, the receptacle 20 comprises a housing 30 defining a volume 70, an inlet 31 and an outlet 32 for ingress and egress of a sample under test into the housing volume, and two transparent windows 21a, 21b on each side of the housing/volume (one is visible) for transmission of electromagnetic radiation into a sample in the volume and subsequent emission of the affected electromagnetic radiation to a detector 17.

Figure 4A:
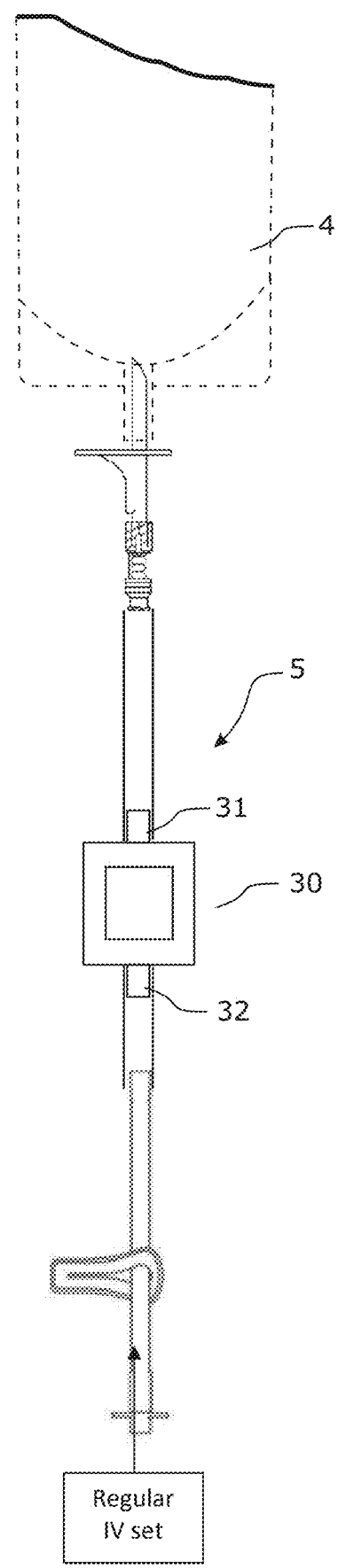
FIGS. 4A/4B shows the sample receptacle according to the first embodiment in use in an IV line with IV bag.
Figure 4B:
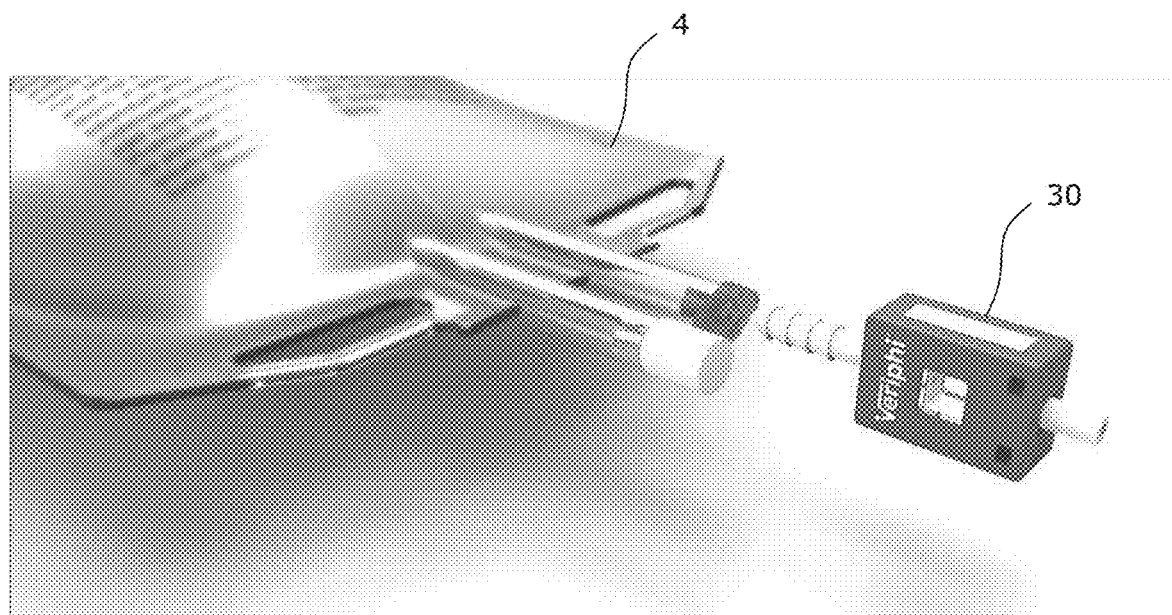
FIG. 4C shows the sample receptacle according to the first embodiment in use in a syringe.

Referring to FIGS. 4A/4b, as an example, the receptacle 20 can be connected to an IV line 5 of an IV bag containing a drug to be characterised. The receptacle inlet 31 is connected to one portion of the IV line that is fluidly coupled to a spike insertion into the IV bag 4 and the outlet 32 is coupled to another portion of an IV line which is fluidly coupled to an IV set. The sample in the receptacle can then be tested in situ with the IV bag/Line. In another option shown in FIG. 4C, the receptacle can be connected to a syringe 151 and sample tested in situ.

FIG. 5 shows the receptacle 20 in further detail—the receptacle comprising various components. The receptacle 20 has a housing 30 comprising two opposing body components 59 that clip together to form part of the housing (one is shown in FIG. 5, the other component is identical). Each body component 59 has a window panel 50 and a perpendicular end panel 51 extending from the end of the window panel. The end panel 51 comprises an opening 53 defined by two tabs 54a, 54b at each side of the end panel. A lateral nib wall (one is shown 55a in the perspective view, the other is identical) extends along and at right angles from each longer edge of the window panel 50 to form a partial side wall on each side of the window panel. A vertical nib wall (one is shown 56a in the perspective view, the other is identical) extends at right angles from and along the end panel and is integrated with it.

An internal wall 57 extends perpendicularly from the inner surface 50b of the window panel 50. The internal wall comprises an opening 58 defined by two tabs 58a, 58b at each side of the wall, each tab finishing at a locking clip 40. The window panel 50 comprises two recesses 41a, 41b at one end for receiving the tabs 54a, 54b from the end wall 51 of the corresponding opposing body component, and two apertures 42a, 42b at the other end for receiving the locking clips 40 from the inner wall 57 of the corresponding opposing body component. Each window panel 50 has an outer surface 50a, and inner surface 50b. The outer surface is predominantly flat profile, although has profiling around the edges and other apertures to be described below. The inner surface is profiled with a protruding frame 43 to locate and retain one of the transparent windows 21a, 21b.

When assembled, the openings 53, 58 of the end panel 51 and inner wall 57 combine with the opposing body's corresponding inner wall opening and end panel opening respectively for receiving the inlet 31 and outlet 32 respectively. The two opposing body components can be clipped and assembled together, such that the tabs 58a, 58b of the inner wall 57 and tabs 54a, 54b of the end panel 51 of a first opposing body component couple to the recesses 41a, 41b and apertures 42a, 42b respectively of the second opposing body component. When assembled, the first and second opposing window panels also define an opening (one is shown 44) on each side of the housing for receiving part of a support frame 46 to now be described.

The support frame 46 forms part of the receptacle, preferably forming part of or being disposed in the housing 30. The support frame (more generally "support") comprises an outer frame 47 with an internal block 48 with an opening defining a volume 70. Each side of the block (one side is shown) has a recess 49 for seating of a compliant member 80. As shown, one example of a compliant member could be a silicon or other resilient ring. The compliant member is seated and over moulded in the recess 49. One compliant member is shown, but it will be appreciated that there is another compliant member on the other side. The inlet 31 and outlet 32 conduits extend from opposing sides of the frame 46, each with an internal channel that fluidly couples to the volume 70 in the internal block 48. A window sits (21a is shown) on each compliant member 80 covering the volume, to provide two opposing windows separated by a gap of 2 mm+/−0.2 mm (being the thickness G1 of the internal block 48 across the volume) to provide the volume for a sample. Each window sits in the frame 43 on the internal side of the window panel. Each transparent window could be a quartz crystal window with the transmission characteristics in the 1300 to 2000 range (as just one non-limiting example—the window could be manufactured for any suitable transmission characteristics), and is manufactured to have a thickness W1 or W2 of 3 mm+/−0.1 mm. This provides a total path length P1 of 8 mm+/−0.4 mm. A sample 11 to be tested can ingress through the fluid channel of the inlet 31 into the volume 70, and egress from the volume 70 through the channel of the outlet 32.

The receptacle 20 is assembled by clipping the first and second opposing body components 59 together over the support frame 46. The inlet 31 and outlet 32 conduits extend through the apertures 58, 53 in the first and second opposing end panels/internal walls, and the first and second opposing windows are exposed through the apertures in the first and second opposing window panels. The windows 21a, 21b, can travel towards and away from the inner surface 50b of the window panel within the frame 43, under external force F as constrained by the compliant member 80 to control the gap thickness G1. Optionally, the compliant member 80 holds the transparent windows 21a, 21b in position between the inner side of the first and second opposing windows and the corresponding compliant member.

Figure 6:
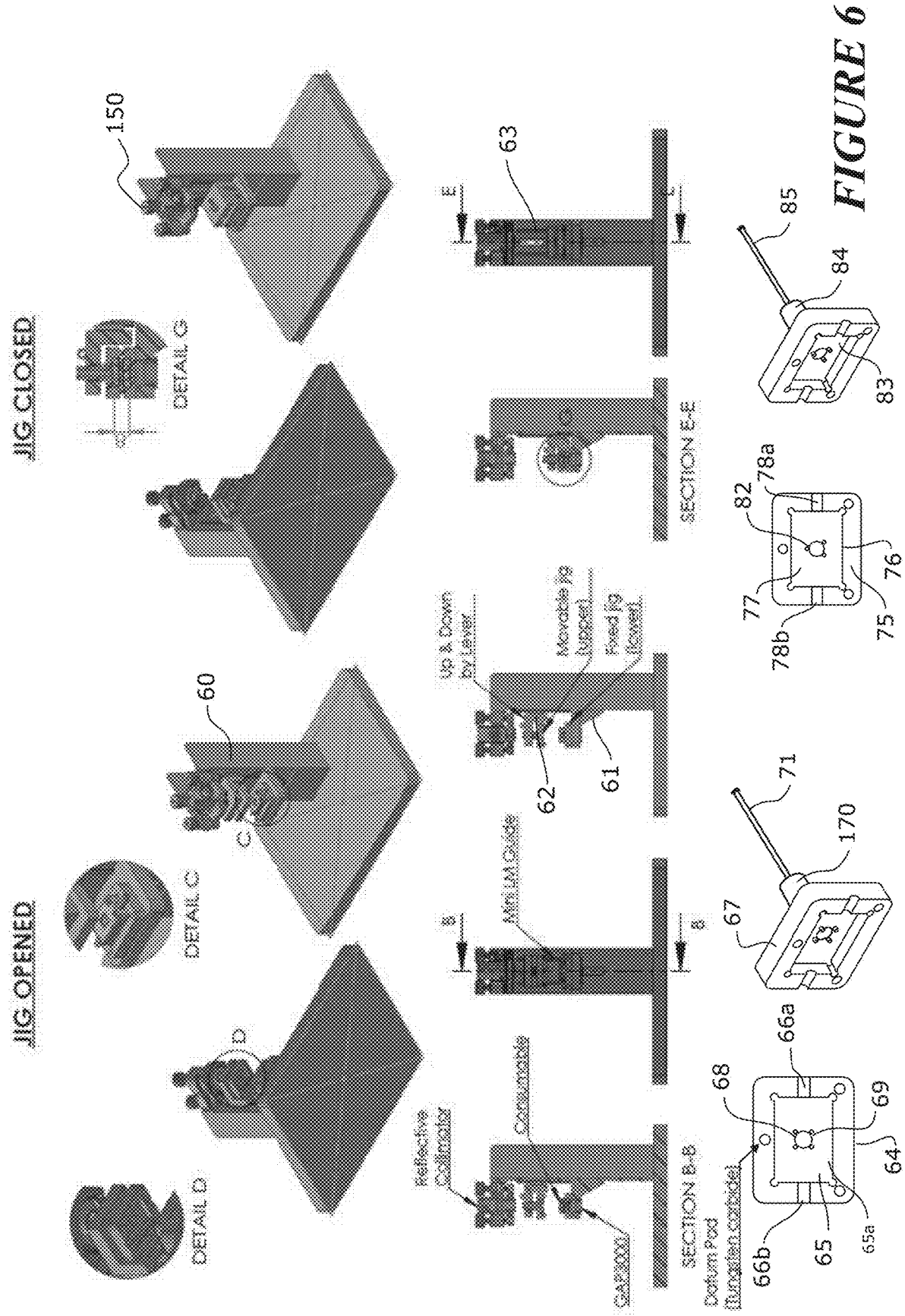
FIG. 6 shows a jig for use with or forming part of the sample receptacle.

The housing 30 is dimensioned to be received in a jig (also termed "holder"), such as in FIG. 6. The jig or part of the jig can optionally be considered to be part of the receptacle, or alternatively separate to it depending on context and/or the embodiment. The jig comprises a platform with a vertical upstand 60, lower fixed jig platform 61 and upper movable support 62 that can slide vertically up and down the upstand 60 by way of protrusions that run in tracks 63 fabricated into the upstand. The lower fixed jig platform 61 supports a lower fixed jig 64. The lower jig 64 comprises a block 67 with a recess 65 dimensioned to receive one half of the receptacle housing 30. Two semi cylindrical channels 66a, 66b formed in the side walls of the block 67 to receive half of the inlet 31 and outlets 32 of the receptacle 30. The bottom surface 65a of the recess comprises an aperture 68, and a datum 69 in the form of two protrusions either side of the aperture that form a stop. The bottom of the block has a connector 170 for connection to a channel 71 for carrying electromagnetic radiation from the aperture. For example, the connector could be for a fibre-optic channel for connection to the controller to carry electromagnetic radiation to the detector 17.

Similarly, the upper movable jig 62 support supports an upper jig 75. The upper jig 75 is similar in nature to the lower jig 64 and comprises a block 76 with a recess 77 dimensioned to receive one half of the receptacle housing 30. Two semi cylindrical channels 78a, 78b are formed in the side walls of the block to receive half of the inlet 31 and outlets 32 of the receptacle. The bottom surface of the recess 77 comprises an aperture 82, and a datum 83 in the form of three protrusions either side of the aperture that form a stop. The bottom of the block has a connector 84 for connection to channel 85 for carrying electromagnetic radiation to the aperture from the source. For example, the connector could be for a fibre-optic channel for connection to the output of one or more lasers. It will be appreciated that the datums could take any physical structure such as protrusions or the like to form a stop, and those described by way of example only.

A reflective collimator 150 is provided that receives incident light from a fibre and collimates it for transfer to the upper jig.

The fixed jig 64 and upper moveable jig 75, along with the rest of the jig apparatus, are reusable, and can be manufactured using a more costly and/or complex process that provides a higher degree of tolerance/precision. Therefore, the jigs 64, 65 can be manufactured so that the datum is dimensioned to a high degree of accuracy. The receptacle housing 30, and support frame 46 are disposable/consumable. They are disposed of after each test (one time use), or possibly after a number of tests. They are manufactured using a cheaper process which allows for this. This results in a receptacle housing 30 manufactured to a lower degree of precision, but this can be compensated for by use of the jigs as will be described. The quartz windows 21a, 21b are preferably manufactured to a high tolerance, but even if not, the overall path length P1 can be achieved to the required tolerance using the jigs as to be described. While it is preferable that the windows are manufactured to 3 mm+/−0.1 mm, deviation from this is not as crucial, as long as the overall path length P1 of 8 mm+/−0.4 mm can be achieved.

Use of the receptacle 20 in the spectrophotometer system 10 will now be described. The use will be described in relation to characterising drugs in a pharmacology unit of a hospital or similar, although this is by way of example only and the receptacle could be used in other contexts as will be appreciated by those skilled in the art.

Referring to FIG. 3, the receptacle housing 30 is assembled and then connected to the IV line 5 of an IV bag the drug to be characterised, see FIG. 4A/4B. When the IV line is spiked into the bag a portion of the drug (sample) enters the volume 70 and the receptacle 20 between the two opposing windows 21a and 21b. At this point there is no flow on the line (there is a valve, clip or similar in the line), so the portion of drug (sample) 11 in the volume 70 is static. The housing 30 of the receptacle is then placed in the recess 65a of the lower fixed jig 64. Referring to FIG. 7, the datum 69 on the lower jig 64 protrudes through the aperture in the face of the housing 30 and rests against the window 21a. The upper movable jig 75 is then lowered into position by sliding the jig support 62 down the rails 63 on the upstand, until the datum 82 on the upper movable jig 75 protrudes through the aperture on the opposing face of the housing to rest against the other opposing window 21b. The support continues to slide until the walls/frame of the upper movable jig and the lower movable jig abut against each other and clamp around the housing and inlet/outlet.

Once the jig is in position, the distance P1 between the protrusions of the first 69 and second 83 datums will provide the desired path length P1 distance (e.g. 8 mm+/−0.05 mm) to the required level of tolerance between the outer surfaces of the two opposing transparent windows. That is, the distance between the datums 69, 83 provides the required path length to the required tolerance. The compliant members 80 provide a reaction/biasing force that allows movement of each respective window so it can be positioned correctly under the external force of the respective datum, while still being held against the datums. (The pressure of the sample might also add some outward force.) The action of doing this will position the first and second opposing windows 21a, 21b at the required distance apart so that the gap G1 between them is preferably the desired distance to the required tolerance (e.g. 2 mm+/−0.2 mm)—assuming the window thicknesses W1, W2 are within the required tolerance (which they would be if manufactured to the desired precision). Even if the window thicknesses are not to the desired precision (e.g. 3 mm+/−0.1 mm) as described above, this is not as critical and can be compensated for by the datum and ensuring the whole path length P1 is the desired length to the required tolerance. As such, the jig can compensate for tolerance deficiencies which might otherwise result in a gap G1 that falls outside the desired range, or a path length P1 that falls outside the desired range.

The first 69 and second 83 datums are also fabricated to a high degree of flat orientation so that upon coming together they will position the first and second opposing windows 21a, 21b in the desired parallel orientation (or any other desired orientation)—e.g. to within +/−0.05 degrees of parallel and also perpendicular or substantially perpendicular to incident radiation, in use. The compliant member 80 on each side compensates for any manufacturing tolerances in the window, or in the support, so that each window can be positioned under force against the datum and therefore positioned to set the required a) gap between the first and second opposing windows, and/or b) relative orientation of the first and second opposing windows, and/or overall path length.

The electromagnetic source, such as one or more lasers, can be coupled to the first upper jig 75, e.g. by way of fibre-optic cable 85 through connector 84, and likewise to the output 71 of the lower jig 64 can be coupled via channel 71 to the detector 17, e.g. by way of fibre-optic cable. Preferably, the collimator 150 is provided, so that the fibre-optic cable 85 goes to the collimator which first collimates the light, for transfer to the connector 84 in the upper jig 75. Testing can then begin.

The analyser 20 can then be operated to characterise the sample in the receptacle, for example in a manner described in the aforementioned patent publications. Once analysis is complete, the receptacle housing 30 can be removed from the jig, the housing dismantled and/or the receptacle removed from the IV line. The disposable parts are thrown away.

A benefit of the receptacle described is that the disposable portion of the receptacle, being the housing, window, support and/or compliant member can be fabricated using a cheaper process that does not necessarily have the required degree of tolerance to provide the required degree of gap, path length and or parallel orientation of opposing windows. The jig, including the upper and lower jigs, can be manufactured using a different process that provides a high degree of tolerance. Using the jig manufactured to a high degree of tolerance, any manufacturing tolerances due to the cheaper process in the consumable part of the receptacle can be compensated for by the more precisely manufactured jig. As the jig is not a consumable item, it is commercially feasible to manufacture it using a more costly, but precise process. Because the receptacle housing and other components are consumable, it is desired to manufacture them using a cheaper process, even if that cheaper process does not manufacture to the required precise tolerances.

Figure 9:
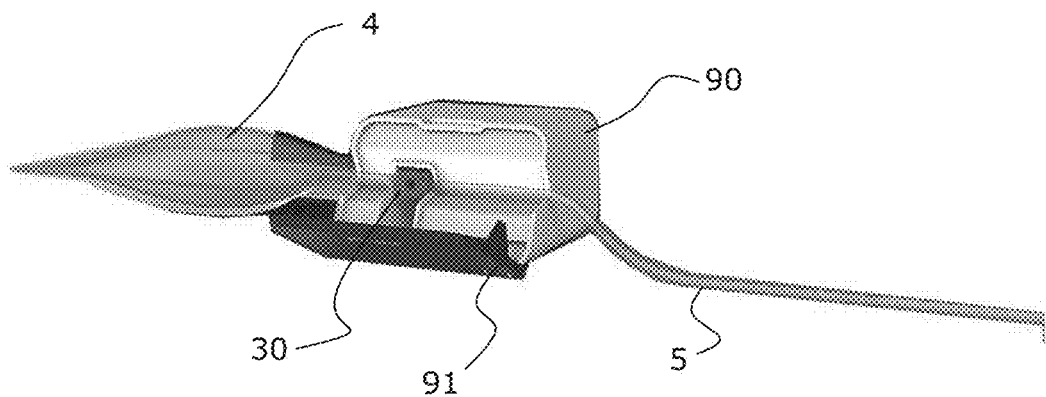
FIG. 9 shows example embodiment of a testing unit with a holder for receiving a sample receptacle.

The jig embodiment described above could be used in a manual bench top situation, where a clinician or other user operates the jig to carry out tests. The jig could also be automated to automatically insert a receptacle into the jig, operate the jig, carry out a spectrophotometry test, and/or extract the receptacle from the jig. FIG. 9 shows an example embodiment wherein the receptacle (when attached to an IV line/bag such as shown in FIGS. 4A/4B) can be inserted into a test unit 90. This test unit incorporates a holder/jig that operates and has features like that described previously. The front cover 91 can hinge shut to create movement of one portion of the jig (e.g. equivalent of the upper jig 75 described previously which could be incorporated into the lid) over the receptacle to set the parameter distances as described earlier. Other parts of the jig such as the lower jig can be in the test unit body. The test unit can optionally also house or be connected to the overall spectrophotometry system 10, or part thereof; or it can just provide the jig functionality. Other embodiments of a test unit incorporating a holder could also be used. A holder like that described above generally, or in particular embodiments, can be incorporated into any suitable test unit.

This is just one example, and other examples could be envisaged whereby a more precisely manufactured datum(s) is/are used on a reusable/non-consumable part of receptacle, and a cheaper less precise manufacturing process can be used on the consumable portion. For example, the receptacle could comprise a housing with an external or internal datum or datums manufactured as a stop to a precise degree. Under force, a consumable item comprising opposing windows supported on one or more compliant members separated by a gap to form a volume, can be positioned against the stops to provide the required gap, path length and parallel orientation. For example, the housing itself could contain the datum/s and be reusable, and the support, window and compliant members are consumable. Other variations are possible also. It will be appreciated that a receptacle (and optionally external jig or similar) can be designed so that the components such as datum that require fabrication to a high tolerance can be made reusable, and the consumable portions can be fabricated from a cheap less precise method, while still ensuring the key receptacle parameters are within the required tolerances.

Figure 8A:
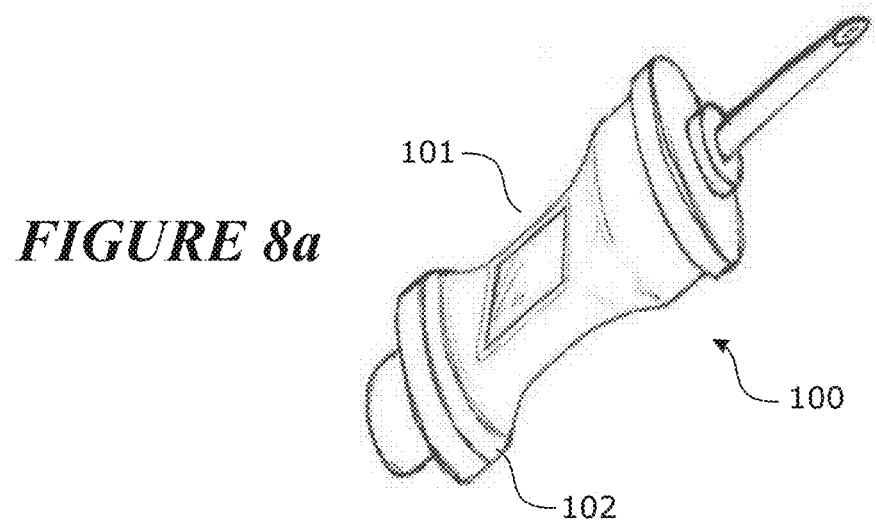
FIGS. 8*a* to 8*d* show an alternative embodiment of a sample receptacle.
Figure 8B:
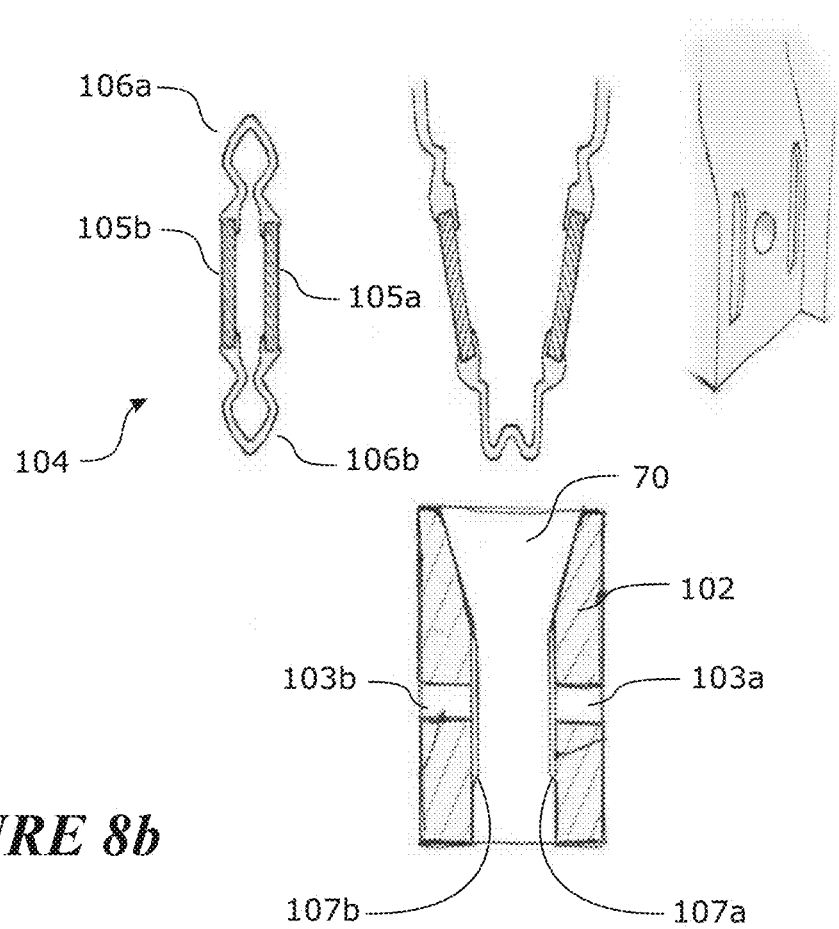

By way of example another embodiment is shown in FIGS. 8a to 8d. Here the receptacle takes form of a solid housing 102 with a concave exterior 101. A profile of the interior 70 is shown in FIG. 8b. An aperture is formed opposing sides 103a, 103b in the hollow concave area. A datum 107a, 107b in the form of a rail is provided by each aperture—forming respective stops. The datums are manufactured to a high degree of tolerance in the housing so that the distance between them is P1—e.g. 8 mm+/−0.05 mm, and so they are parallel to within +/−0.05 degrees and perpendicular or substantially perpendicular in use to incident radiation. The housing 102 and datums can be reusable. A window insert 104 is provided comprising transparent windows 105a, 105b (such as quartz windows with the required thickness W1, W2 as described earlier). The windows are held together at each end with compliant hinges 106a, 106b. The hinges can be made from silicon or other compliant material. They can be manufactured cheaply and can be disposable, along with the windows 105a, 105b. The window insert 104 can be provided into the interior 70. The compliant hinges 106a, 106b bias the windows 105a, 105b against the respective datums 107a, 107b. This positions the windows 105a, 105b so that they are parallel to the required degree, arranged at right angles to incident radiation to the required degree, and the gap G1 is 2 mm+/−0.2 mm and P1 is 8 mm+/−0.4 mm. Again, the compliant members in combination with the datums allow a cheaper manufacture of the window insert 104 to provide for disposability of the windows 21a, 21b and compliant members 106a, 106b, while still ensuring the receptacle parameters are to the required tolerance due to the manufacture of the reusable housing 102 and datum to a high degree of tolerance.

Figure 8C:
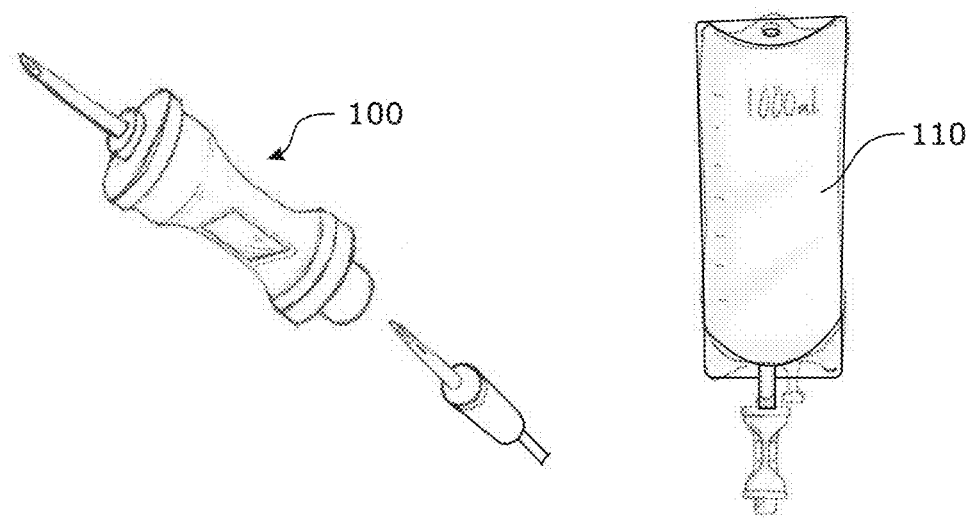
Figure 8D:
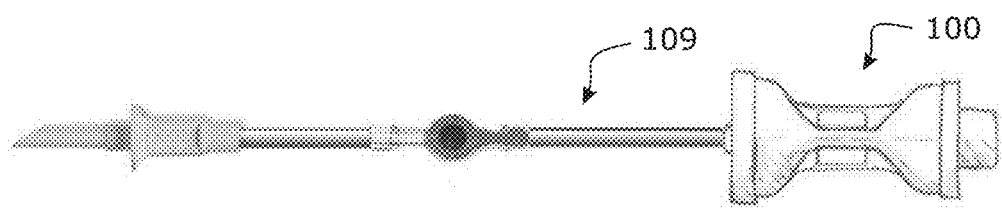

Referring to FIGS. 8c, 8d, the receptacle can be incorporated into the IV line 109 of an IV bag 110.

Figure 4C:
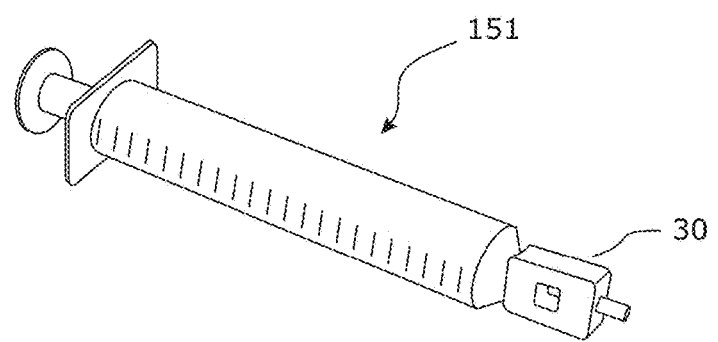

Referring to FIG. 4C, the receptacle and holder above could be connected to and used for a syringe 151 delivery of a drug instead.

In other embodiments, it is not necessary for the receptacle to be connected to a syringe or IV bag and tested in situ. The receptacle (with sample) could be used alone separate from the delivery apparatus and inserted into the holder for testing.

By way of a further example, yet another embodiment is shown in FIGS. 10 (10-I, 10-II) to 11. In this embodiment, the receptacle 120 is formed as a compliant/resilient frame/body 121 that supports the windows 123A, 123B in a compliant manner. It is used with a jig 140 such as that shown in FIG. 11. The receptacle 120 can be manually or automatically inserted into the jig 140, which coerces the windows into a position to provide the receptacle parameters and tolerances as previously described. The receptacle 120 provides the cheaply manufacturable disposable/consumable part of the arrangement, and the jig 140 provides the reusable component manufactured to the required degree of tolerance. The two components together provide the required parameters for spectrophotometry testing to the desired tolerance. As with the previous embodiments, the jig 140 or part of the jig can optionally be considered to be part of the receptacle 120, or alternatively separate to it depending on context and/or the embodiment.

Referring to FIG. 10, the further example embodiment of the receptacle 120 will be described in more detail. The receptacle 120 comprises a body/frame 121, which itself comprises a support frame 122 for supporting the windows 123A, 123B. The support frame 122 is of generally planar geometry for supporting the windows, and is formed from a resilient/compliant material, such as:

silicon
rubber
or any other thermoplastic elastomer

Optionally, the support frame 122 is bookended by two guides 124A, 124B, such as abutments or other end portions that are disposed on each end of the support frame 122. The end portions 124A, 124B are arranged to extend perpendicularly with respect to the support frame 122 to assist with holding and manipulation of the receptacle; and insertion and location of the receptacle into the jig 140. Each end portion 124A, 124B could take a semi spherical form, with an abutment/guide surface 125A, 125B. Other configurations are possible, such as planar plates or the like. The end portions themselves can be formed of the same resilient/compliant material—preferably the same as the support frame, or may be formed from different materials such as a polymer or hard plastic material.

The support frame 122 (more generally "support") is a resilient/compliant block with a recessed internal block 126 that has a recess 126A on each side and has an opening/aperture 127 defining a volume 70. Inlet 128 and outlet 129 channels are formed in the frame (and/or form part of the opening) and extend to opposing sides of the frame. Inlet and outlet conduits 130, 131 (131 is shown in the perspective view but an equivalent conduit is in the other end portion) are formed in the end portions 124A, 124B and fluidly coupled to the volume 70 in the internal block 126 via the inlet/outlet channels 128, 129 to allow ingress and egress of fluid into the volume 70. The inlet/outlet conduits 130, 131 can have external couplings for coupling to a delivery device or syringe such as previously described.

Each side of the block 126 (one side is shown) is provided with recesses 126A with respect to the outer frame support 122 to create a seat (to form the recessed internal block) for locating and seating a respective window 123A, 123B. Each window 123A 123B can be retained in place by friction fit, an overmould, a sealant material and/or other means such as a physical restraint and/or adhesive, for example. The recessed block 126 has a thickness to receive the window, preferably 2 mm+/−0.2 mm, and the volume/aperture 70 has the same thickness. The windows 123A, 123B are compliantly received and retained in each recess to cover the volume 70, to provide two opposing windows separated by a gap of 2 mm+/−0.2 mm (being the thickness G1 of the internal block 126 across the volume) to provide the volume 70 for a sample. Each window 123A, 123B can move under external force, from e.g. the rig 140, into position to achieve the desired parameters for spectrophotometry, wherein the compliance of the recessed block 126 allows for movement of the windows. Each transparent window could be a quartz crystal window with the transmission characteristics in the 1300 to 2000 range (as just one non-limiting example—the window could be manufactured for any suitable transmission characteristics), and is manufactured to have a thickness W1 or W2 of 3 mm+/−0.1 mm. This provides a total path length P1 of 8 mm+/−0.4 mm (being the combination of the windows W1, W2 and the gap G1 as previously described). The perimeter edges of the windows can be tapered, so when retained in each recess of the support member, a channel is formed around the perimeter of the window and the recess into which a sealant can be provided to seal the volume.

A sample 11 to be tested can ingress through the inlet conduit 128 and channel 130 into the volume 70, and egress from the volume 70 through the outlet conduit 129 and channel 131.

It will be appreciated that the direction of ingress/egress is not fixed, so the inlet/outlet channels/conduits could be swapped and/or perform either function.

The jig 140 is manufactured from a rigid material such as:
Steel, preferable stainless steel
A polymer
Or other good thermal coefficient material that has minimal thermal expansion.

that can be reusable and manufactured to a high degree of tolerance. The jig comprises a base 141 with two opposing lateral extensions/guides 142A, 142B forming a slot/gap 143 for receiving the support frame 122/windows part 123A, 123B of the receptacle 120. The extensions 142A, 142B are manufactured to a high degree of tolerance to provide internal faces 144A, 144B so that there is a gap of 8 mm+/−0.4 mm between the internal faces 144A, 144B of the extensions/guides 142A, 142B to provide the total path length P1. The ends of the lateral extensions may be tapered, chambered or otherwise configured 145A, 145B to assist insertion of the receptacle 120 into the gap 143. Openings/couplings 146 (one side shown in perspective, another opening/coupling is on the other side) are provided through each lateral extension 142A, 142B to allow for coupling of an optical fibre or other optical channel to couple electromagnetic radiation from the emitter and to the receiver on each side.

The lateral extensions 142A, 142B could have a flat/planar continuous internal face, but preferably each is formed/configured to have a central recess 147A, 147B with raised faces/surfaces 144A, 144B on either side to provide rails 148A to 148D. The raised faces form the internal faces and are configured and positioned to provide the gap/path P1 length. The rails 148A to 148D/central channel 147A, 147B are provided so that, when inserted into the jig, only edges/side parts of each window 123A, 123B in the receptacle slide and abut against the internal face (on the rails) of the lateral extensions, thus reducing wear and tear, scratching or other abrasions on the windows 123A, 123B that might affect measurement. The optical openings/couplings 146 are positioned in the central recesses 147A, 147B. This leaves a clear optical path for spectrophotometry.

The raised faces 144A, 144B (rails 148A to 148D) provide first and second datums to retain each window 123A, 123B in place. The distance P1 between the faces 144A, 144B of the first and second datums will provide the desired path length P1 distance (e.g. 8 mm+/−0.05 mm) to the required level of tolerance between the outer surfaces of the two opposing transparent windows 123A, 123B. That is, the distance between the datums 144A, 144B provides the required path length to the required tolerance. The compliant support frame 122 provides a reaction/biasing force that allows movement of each respective window 123A, 123B so each can be positioned correctly under the external force of the respective datum, while still being held against the datums. (The pressure of the sample might also add some outward force.)

The action of doing this will position the first and second opposing windows 123A, 123B at the required distance apart so that the gap G1 between them is preferably the desired distance to the required tolerance (e.g. 2 mm+/−0.2 mm)—assuming the window thicknesses W1, W2 are within the required tolerance. Even if the window thicknesses are not to the desired precision (e.g. 3 mm+/−0.1 mm) as described above, this is not as critical and can be compensated for by the datum and ensuring the whole path length P1 and/or G1 are the desired length to the required tolerance, by altering the gap G1 due to the compliance of the support frame. It will also place the windows at the required orientation relative to each other and the incident radiation in use.

In use, the analyser apparatus will be arranged as best as possible to provide incident radiation perpendicular to the opposing window surfaces. The first 144A and second 144A datums are also fabricated to high degree of flat orientation so that upon coming together they will position the first and second opposing windows 123A, 123B in the desired parallel orientation (or any other desired orientation)—e.g. to within +/−0.05 degrees of parallel and perpendicular or substantially perpendicular to the incident electromagnetic radiation. This will allow for adjustment to compensate in any error in the analyser apparatus setup so that the optical path/incident radiation through the windows to follow a straight line at right angles relative to the windows' surfaces such that the angle of incidence of the electromagnetic radiation on the first window will be the same as the angle of incidence on the second window. This angle of incidence being as close as possible to 90 degrees+/−0.05 degrees. The compliant support frame 122 compresses on each side, under force from the datums on the jig, to change the thickness to compensate for manufacturing tolerances in the window, or in the support frame 122, so that each window can be positioned under force against the datum and therefore positioned to set the required: a) gap between the first and second opposing windows, and/or b) relative orientation of the first and second opposing windows, and/or overall path length.

The length of the support frame of the receptacle and the end portions are arranged such that the distance therebetween matches the width of the lateral extensions so that the receptacle can be snugly inserted in and retained in position with a friction fit in the gap between the lateral portions with minimal movement.

The jig can be a standalone item, or can be formed into a testing unit, such as that in FIG. 9, in which the receptacle can be automatically or manually inserted into the jig, such as previously described. The apparatus is arranged so that the angle of incidence of incoming/incident radiation is as close as possible to right angles/perpendicular relative to the window surfaces.

The embodiment above is described as having two windows, each on a side of a compliant support frame, such that the frame can compress under force from both sides to compensate for tolerances. It is possible that either only one side with one window is compressed under external forces, and/or only one side of the support frame is compliant. This would result in tolerances being compensated by only movement of one of the windows under external force.

Figure 13:
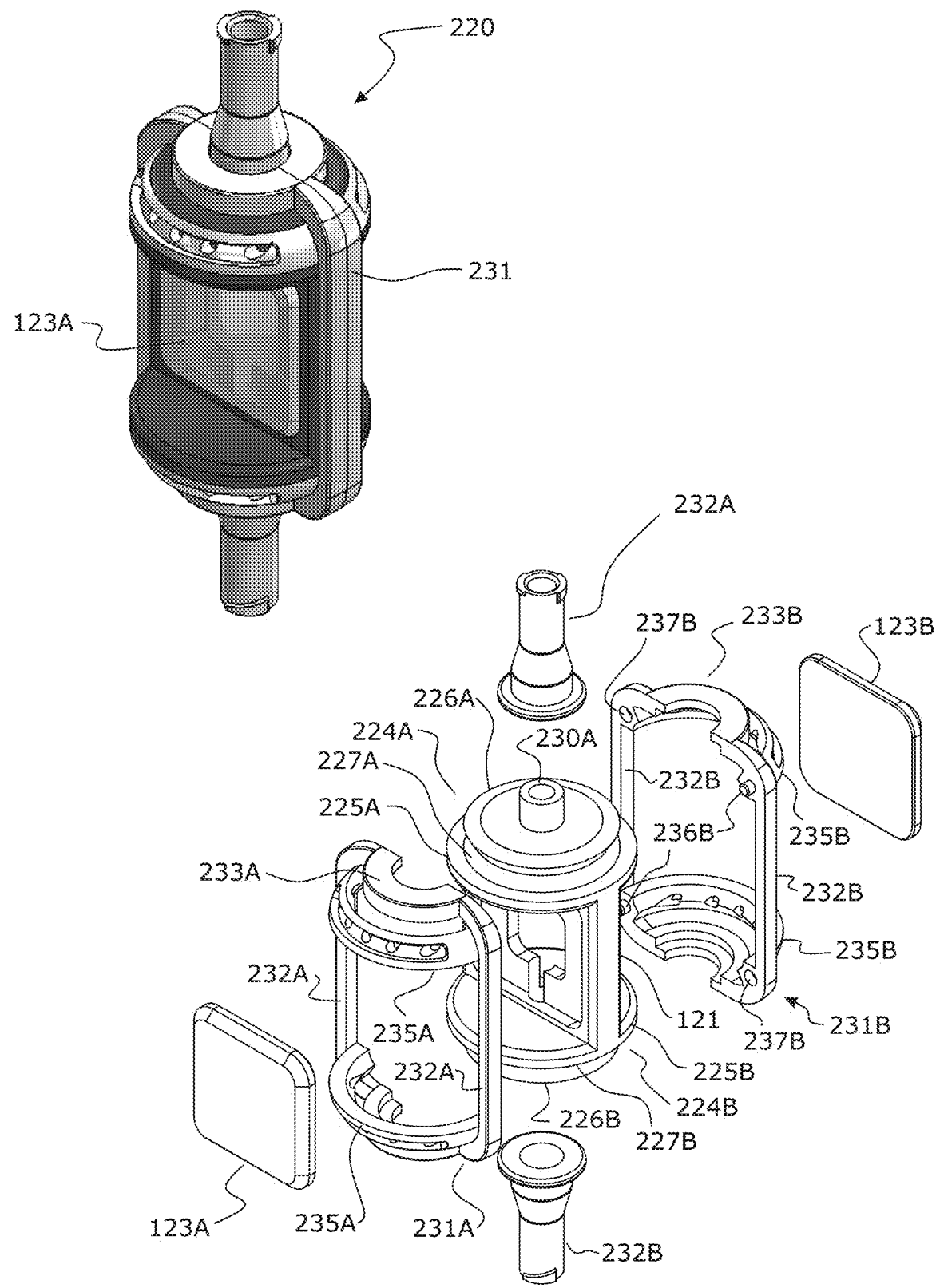
FIGS. 13 and 14 shows a further alternative embodiment of a sample receptacle and jig.
Figure 14:
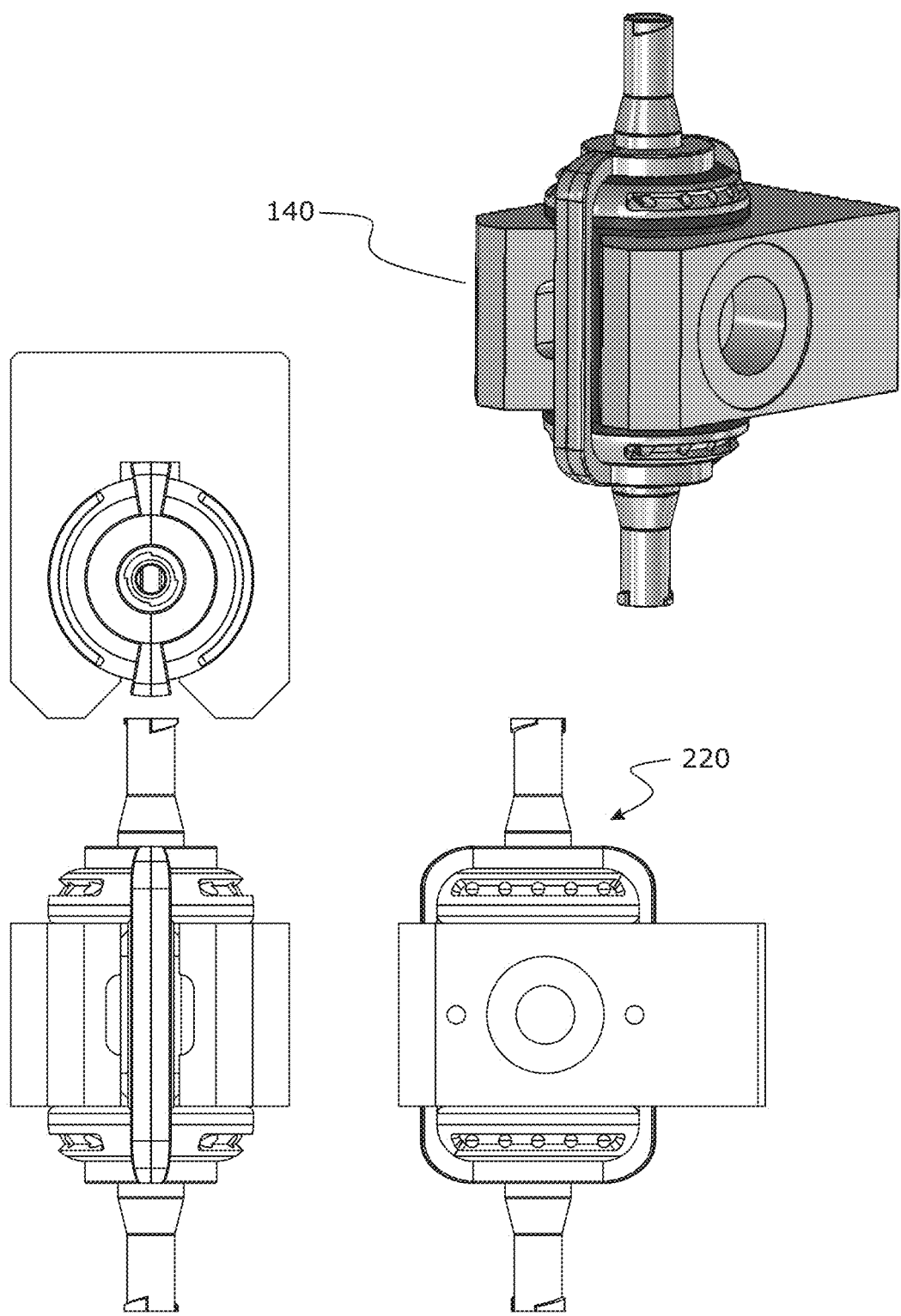
Figure 15:
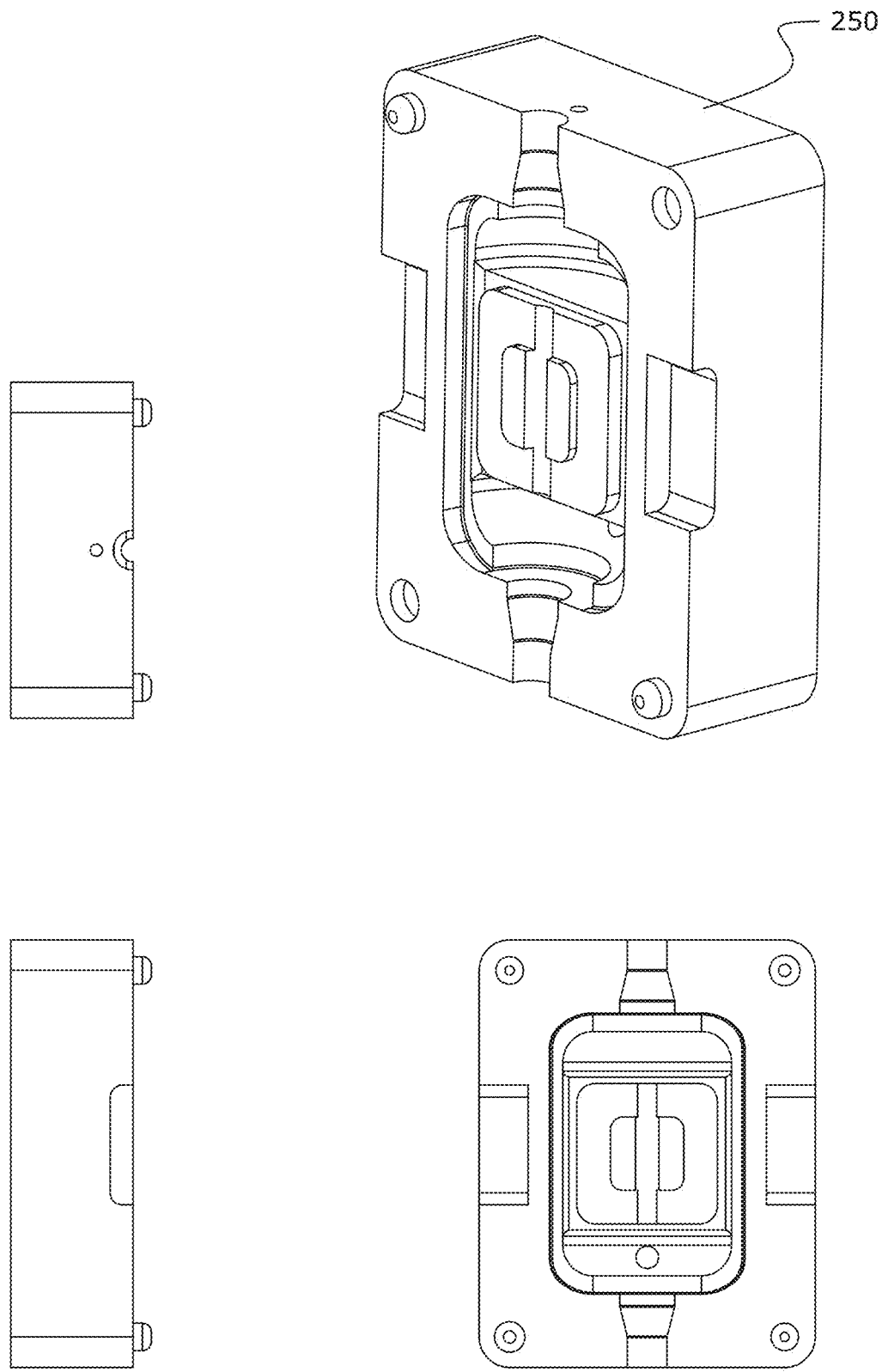
FIG. 15 shows a mould for the embodiment of FIGS. 13, 14.

A variation of this embodiment is shown in FIGS. 13 to 15. This receptacle 220 is similar in nature to that of FIGS. 10 to 11, except that there is an exoskeleton/external frame 231 over the body 121 to provide rigidity. The body 121, window 123A, 123B and other features are as described previously, except for differences now to be described. In FIG. 13, external inlet/outlet extensions 230A are shown moulded as part of the body. Inlet/outlet tubular couplings 232A, 232B can be coupled to the extensions 230 to allow for connection to IV line/bag, syringe or the like. The end portions 224A, 224B have their circumference profiled to provide an annular seat 225A, 225B spaced apart from an annular lip 226A, 226B by an engagement channel 227A, 227B to provide a coupling for the frame. The frame is formed of two frame halves 231A, 231B that are brought together to be secured around the body 121. Each frame half comprises a frame perimeter with two longitudinal side members 232A, 232B coupled together by semi-circular end couplings 233A, 233B at each end. The semi-circular end couplings have a radius commensurate with the outside diameter of the tubular couplings 232A, 232B to allow for inter-engagement. The frame 231 also comprises semi-circular body couplings 235A, 235B towards each end between each longitudinal side member, which have a radius commensurate with the engagement channel 227A, 227B to enable the frame 231 to couple to the body 121. The body couplings comprise apertures for manufacturing purposes. Each frame half 231A, 231B also has locating protrusions (236B shown) and corresponding locating apertures (237B shown) for receiving the protrusion of the other frame half.

The two frame halves 231A, 231B together capture the body 121, located by the protrusions/apertures and clipped or otherwise secured together, such that at each end the respective semi-circular end couplings 233A, 233B join to secure around the tubular couplings 232A, 232B, and the respective semi-circular body couplings 235A, 235B join to secure around the engagement channel 227A, 227B. The assembly can then be inserted into a jig 140 and a test carried out as previously described—see FIG. 14.

Referring to FIG. 15, during manufacture, the body is formed using "inset moulding". One half of the mould 250 is shown in FIG. 15. Firstly, the two part external frame 231 is formed, then one half 231a, 231B of the external frame is placed into one half of the mould 250, the other half into the other mould. Connectors can be put into place, and a long cylindrical member is placed through the connectors to form a channel (inlet/outlet) through which the fluid sample can flow when the receptacle is put into use. The two mould halves are bought together and a rubber or other pourable material is then poured into the mould, where the rubber flows in and around the external frame—so that it ends up being one single piece body 121. The rubber cures and the windows can then be put in place.

The frame provides rigidity to the overall body 121 of the receptacle 120.

Another variation of the embodiment shown above is shown in FIG. 12, which also has rigid frame. In this embodiment, the receptacle 160 is formed as a rigid frame/body 161 that has a resilient/compliant a covering 180, such as a sheath, over-moulding or the like that supports the windows 163A, 163B in a compliant manner. It is used with a jig (holder) 140 such as that shown in FIG. 11 and as previously described. The receptacle body/frame comprises a rigid support frame 162 for supporting the windows 163A, 163B. The support frame 162 is of generally planar geometry for supporting windows. Optionally, the support frame is bookended by two rigid guides 164A, 164B, such as abutments or other end portions that are disposed on each end of the support frame 162. The end portions are perpendicularly arranged to assist with holding and manipulation; and insertion and location of the receptacle into the jig. Each end portion takes a planar/pate form, with an abutment/guide surface, but other configurations are possible. The body 160 comprising the support frame 162 and end portions 164A, 164B is formed from a rigid material such as:
plastics,
metal The support frame 162 (more generally "support") comprises a block that has an opening/aperture defining a volume 70. Inlet 168 and outlet 169 channels are formed in the frame (and/or form part of the opening) and extend to opposing sides of the frame. Inlet 170 and outlet 171 conduits are formed in and extend from the end portions and are fluidly coupled to the volume 70 via the inlet/outlet channels to allow ingress and egress of fluid into the volume 70. The inlet/outlet conduits can have external couplings (e.g. threads) for coupling to a delivery device or syringe such as previously described.

The compliant/resilient covering 180 comprises a support frame 182 cover portion, and end portion 184A, 184B cover portions with internal geometry to receive and cover the rigid frame 161, with its support frame 162 and end portions 164A, 164B. In one option, the covering is hinged at one side and can be clasped over and secured to the rigid frame 161. Alternatively, the covering can be formed as two separate pieces that attach over and are retained on the rigid frame. The support frame 182 portion of the covering comprises a recessed internal block 186 that has an opening/aperture coinciding with the opening/aperture defining a volume 70. This retains a window as previously describe with reference to FIG. 10 and provides the resilience/compliance as previously described. The combination of the rigid support frame 161 and covering 180 works in the same manner as the previous embodiment, including being insertable into the jig 140 to provide the P1, G1 lengths.

Figure 12:
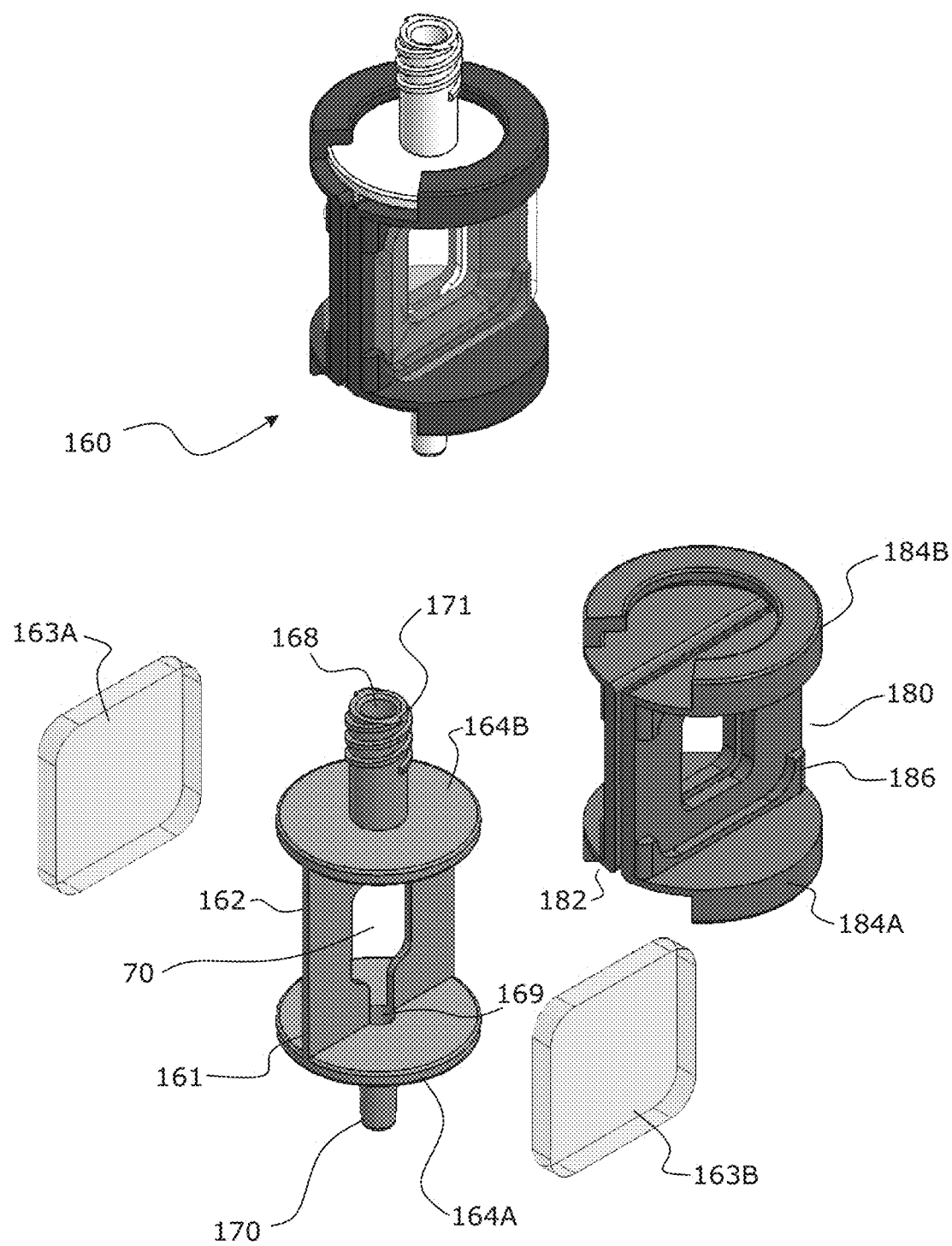
FIG. 12 shows a further alternative embodiment of a sample receptacle.

In use, the receptacle of any of the embodiments of FIGS. 10 and 12 above are coupled to a syringe, IV line, IV bag or other delivery device or sample (e.g. drug) container as previously described—see e.g. FIG. 4A, 4B, 4C, 8C, 8D or 9 for example and related description. A portion of the drug or other sample for test flows into the volume 70 via the inlet conduit and channel. Either before, during or after coupling the receptacle to the delivery device or container and/or releasing sample into the volume, the receptacle is inserted into the gap between the lateral extensions of the jig so that the windows on either side abut against the internal face (e.g. raised rails) of the lateral extensions. The support frame is dimensioned so that when it is pushed all the way down, it abuts the base of the jig, which positions the windows in a vertically aligned manner with the optical openings/couplings. The extensions provide an inward force on the respective windows of the receptacle to squeeze the windows against the compliant support frame to position the windows like that in FIG. 2 such that the core parameters to the required tolerance are achieved. The end portions, which are optional, can provide a guide to assist with inserting the receptacle in position so the windows are aligned with the optical couplings/openings and are retained in place. The end portions and support frame are dimensioned to be spaced commensurate with the width of the extension portions so that there is a good friction fit between the extension portions and the end portions to hold the support frame in a laterally stable manner. The optical channels are coupled to the testing unit, that allows light to pass through the jig containing the receptacle, and spectrophotometry can take place.

The invention claimed is:

1. A receptacle for holding a sample under spectrophotometer analysis comprising:
   a body configured to insert into an external jig that provides a datum with a fixed distance, the body comprising:
   a first compliant member,
   a volume for holding a sample for analysis, and
   first and second opposing windows disposed on opposite sides of the volume and separated by a gap that forms the volume for the sample,
   wherein at least the first opposing window is supported by the first compliant member, and
   wherein when the receptable is inserted into the jig the first opposing window contacts the datum and under a force the first compliant member positions the first opposing window against the datum in the jig to set a desired:
   a) total path length across the first and second opposing windows separated by the gap, and
   b) relative orientation of the first and second opposing windows,
   wherein the jig and compliant member together are configured to compensate for variations in window dimensions due to manufacturing to position the first and second opposing windows so the first and second opposing windows are parallel to within a required tolerance and provide the total path length, due to the fixed distance of the jig, to within a required tolerance.

2. A receptacle for holding a sample under spectrophotometer analysis comprising:
   a body configured to insert into an external jig that provides a datum with a fixed distance,
   a volume for holding a sample for analysis,
   first and second opposing windows disposed on opposite sides of the volume and separated by a gap that forms the volume for the sample, wherein said first and second opposing windows are supported by said body, and
   wherein when the receptacle is inserted into the jig the first and second opposing windows contact the datum, and under a force, the body positions the windows against the datum set to set a desired:

a) total path length across the first and second opposing windows separated by the gap, and b) relative orientation of the first and second opposing windows, wherein the jig and body together compensate for variations in window dimensions due to manufacturing to position the first and second opposing windows so the first and second opposing windows are parallel to within a required tolerance and provide the total path length, due to the fixed distance of the jig, to within a required tolerance.

3. The receptacle according to claim 2, wherein the datum is external to the body.

4. The receptacle according to claim 2, wherein:

the first opposing window is supported by a first compliant member in the body, and/or the second opposing window is supported by a first and/or second compliant member in the body.

5. The receptacle according to claim 2, wherein when the body is received in the jig, the first and/or second opposing windows are positioned by the datum under force of:

a) the sample in the volume, and/or b) the jig moving the datum.

6. The receptacle according to claim 1, wherein the datum comprises one or more stops that the first and/or second opposing windows abut against under force.

7. The receptacle according to claim 1, wherein:

the desired gap is 2 mm+/−0.2 mm, each window is 3 mm+/−0.1 mm thick, and/or the relative orientation between the first and second opposing windows is parallel or substantially parallel to within +/−0.05 degrees, and the orientation of window surfaces is parallel or substantially parallel and/or is substantially at right angles to incident radiation in use within 3 minutes of an arc.

8. The receptacle according to claim 1, wherein the datum is fabricated using a process that allows for a higher degree of tolerance than the process used to fabricate the first and/or second window, first and/or second compliant member.

9. A jig for receiving a receptacle according to claim 1 for holding a sample under spectrophotometer analysis, wherein the holder in use provides a force to the receptacle wherein under the force, the body allows positioning of the first and second opposing windows relative to a datum set to set a desired:

a) gap between the first and second opposing windows, and/or b) relative orientation of the first and second opposing windows.

10. The jig according to claim 9, wherein the datum is in the jig and optionally moveable by the jig.

11. The jig according to claim 10, wherein when a receptacle is received in jig, the first and/or second opposing windows are positioned by datum under force of:

a) the sample in the volume, and/or b) the jig moving the datum.

12. The jig according to claim 9, wherein the datum comprises one or more stops that the first and/or second opposing windows abut against under force.

* * * * *